United States Patent
McCarthy et al.

(10) Patent No.: US 12,097,657 B2
(45) Date of Patent: Sep. 24, 2024

(54) POROUS STRUCTURES PRODUCED BY ADDITIVE LAYER MANUFACTURING

(71) Applicant: Howmedica Osteonics Corp., Mahwah, NJ (US)

(72) Inventors: Thomas Francis McCarthy, Neshanic Station, NJ (US); Brock Miller, Toronto (CA); Robin Stamp, Montclair, NJ (US); Yuri Zaitsev, Nyack, NY (US); Robert W. Klein, Orangeburg, NY (US); Marc Esformes, Fishkill, NY (US); David Markel, Southfield, MI (US); Amit Mistry, Weston, FL (US); Joseph Robinson, Ridgewood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1252 days.

(21) Appl. No.: 16/781,693

(22) Filed: Feb. 4, 2020

(65) Prior Publication Data
US 2020/0171605 A1    Jun. 4, 2020

Related U.S. Application Data

(63) Continuation of application No. 14/969,695, filed on Dec. 15, 2015, now Pat. No. 10,596,660.

(51) Int. Cl.
*A61L 27/56* (2006.01)
*A61F 2/00* (2006.01)
(Continued)

(52) U.S. Cl.
CPC .......... *B29C 64/135* (2017.08); *A61F 2/0063* (2013.01); *A61L 27/56* (2013.01);
(Continued)

(58) Field of Classification Search
CPC ............ A61F 2/0063; A61F 2002/0068; A61F 2002/30914; A61F 2002/30915;
(Continued)

(56) References Cited

U.S. PATENT DOCUMENTS 4,064,567 A    12/1977  Burstein et al.
4,089,071 A    5/1978   Kalnberz et al.
(Continued)

FOREIGN PATENT DOCUMENTS

AU    2008271061 A1 *  1/2010  ....... A61B 17/06109
AU    2018354095 A1    4/2020
(Continued)

OTHER PUBLICATIONS

Aimee, "3D printing custom trachea stents," Shapeways Blog, Aug. 4, 2015, 5 pages, https://www.shapeways.com/blog/archives/21674-3d-printing-custom-trachea-stents.html (retreived on Dec. 9, 2020).

(Continued)

*Primary Examiner* — Tan-Uyen T Ho
*Assistant Examiner* — Osama Nemer
(74) *Attorney, Agent, or Firm* — Lerner David LLP

(57) ABSTRACT

A three-dimensional structure is formed when layers of a material are deposited onto a substrate and scanned with a high energy beam to at least partially melt each layer of the material. Upon scanning the layers at predetermined locations at least a first segment overlapping a second segment and underlapping a third segment is formed.

24 Claims, 16 Drawing Sheets

(51) Int. Cl.
*A61F 2/30* (2006.01)
*B22F 3/105* (2006.01)
*B22F 3/11* (2006.01)
*B22F 10/28* (2021.01)
*B22F 10/366* (2021.01)
*B23K 26/342* (2014.01)
*B28B 1/00* (2006.01)
*B29C 64/135* (2017.01)
*B29C 64/153* (2017.01)
*B33Y 10/00* (2015.01)
*B22F 10/38* (2021.01)
*B29L 31/00* (2006.01)
*B33Y 80/00* (2015.01)

(52) U.S. Cl.
CPC ............ *B22F 3/105* (2013.01); *B22F 3/1103* (2013.01); *B22F 10/28* (2021.01); *B22F 10/366* (2021.01); *B23K 26/342* (2015.10); *B28B 1/001* (2013.01); *B29C 64/153* (2017.08); *A61F 2002/0068* (2013.01); *A61F 2002/30914* (2013.01); *A61F 2002/30915* (2013.01); *B22F 10/38* (2021.01); *B29L 2031/772* (2013.01); *B33Y 10/00* (2014.12); *B33Y 80/00* (2014.12); *Y02P 10/25* (2015.11)

(58) Field of Classification Search
CPC ...... A61F 2002/4415; A61F 2002/4425; A61F 2002/4435; A61F 2002/4495; A61F 2002/30316; A61F 2/00; A61B 2017/00004; A61B 17/68; A61B 2017/564; A61B 17/826; A61B 17/8085; A61L 27/00; A61L 27/04; A61L 27/3608; A61L 27/365; A61L 27/56; B29C 64/135; B29C 64/153; B22F 3/105; B22F 3/1103; B22F 10/28; B22F 10/38; B22F 10/366; B23K 26/342; B28B 1/001; B29L 2031/772; B33Y 10/00; B33Y 80/00; Y02P 10/25

See application file for complete search history.

(56) References Cited

U.S. PATENT DOCUMENTS

| | | | |
|---|---|---|---|
| 4,479,271 A | 10/1984 | Bolesky et al. | |
| 4,570,271 A | 2/1986 | Sump | |
| 4,608,052 A | 8/1986 | Van Kampen et al. | |
| 4,636,219 A | 1/1987 | Pratt et al. | |
| 4,693,721 A | 9/1987 | Ducheyne | |
| 4,715,860 A | 12/1987 | Amstutz et al. | |
| 4,769,041 A | 9/1988 | Morscher | |
| 4,829,152 A | 5/1989 | Rostoker et al. | |
| 4,839,215 A * | 6/1989 | Starling | A61F 2/30756 523/105 |
| 4,863,474 A | 9/1989 | Brown et al. | |
| 4,863,538 A | 9/1989 | Deckard | |
| 4,944,817 A | 7/1990 | Bourell et al. | |
| 4,969,904 A | 11/1990 | Koch et al. | |
| 4,976,738 A | 12/1990 | Frey et al. | |
| 4,990,163 A | 2/1991 | Ducheyne et al. | |
| 4,997,445 A | 3/1991 | Hodorek | |
| 5,013,324 A | 5/1991 | Zolman et al. | |
| 5,017,753 A | 5/1991 | Deckard | |
| 5,030,233 A | 7/1991 | Ducheyne | |
| 5,076,869 A | 12/1991 | Bourell et al. | |
| 5,076,875 A | 12/1991 | Padden | |
| 5,108,435 A | 4/1992 | Gustavson et al. | |
| 5,156,625 A | 10/1992 | Marchetti et al. | |
| 5,234,457 A | 8/1993 | Andersen | |
| 5,368,602 A | 11/1994 | de la Torre | |
| 5,397,359 A | 3/1995 | Mittelmeier et al. | |
| 5,433,750 A | 7/1995 | Gradinger et al. | |
| 5,443,510 A | 8/1995 | Shetty et al. | |
| 5,468,242 A * | 11/1995 | Reisberg | A61B 17/8085 606/151 |
| 5,496,372 A * | 3/1996 | Hamamoto | A61F 2/44 606/907 |
| 5,510,066 A | 4/1996 | Fink et al. | |
| 5,590,454 A | 1/1997 | Richardson | |
| 5,597,589 A | 1/1997 | Deckard | |
| 5,629,077 A | 5/1997 | Turnlund et al. | |
| 5,658,334 A | 8/1997 | Caldarise et al. | |
| 5,662,713 A | 9/1997 | Andersen et al. | |
| 5,711,960 A * | 1/1998 | Shikinami | A61F 2/28 428/36.1 |
| 5,718,159 A | 2/1998 | Thompson | |
| 5,734,959 A | 3/1998 | Krebs et al. | |
| 5,899,935 A | 5/1999 | Ding | |
| 5,926,685 A | 7/1999 | Krebs et al. | |
| 5,948,342 A | 9/1999 | Nakazawa et al. | |
| 5,968,091 A | 10/1999 | Pinchuk et al. | |
| 5,984,926 A | 11/1999 | Jones | |
| 6,031,148 A | 2/2000 | Hayes et al. | |
| 6,093,188 A * | 7/2000 | Murray | A61B 17/8085 606/285 |
| 6,113,640 A | 9/2000 | Tormala et al. | |
| 6,132,674 A | 10/2000 | Compton et al. | |
| 6,146,416 A | 11/2000 | Andersen et al. | |
| 6,204,207 B1 | 3/2001 | Cederblad et al. | |
| 6,206,924 B1 * | 3/2001 | Timm | A61F 2/28 623/17.11 |
| 6,240,616 B1 * | 6/2001 | Yan | A61L 31/146 623/1.42 |
| 6,241,757 B1 | 6/2001 | An et al. | |
| 6,249,952 B1 | 6/2001 | Ding | |
| 6,312,473 B1 | 11/2001 | Oshida | |
| 6,342,068 B1 | 1/2002 | Thompson | |
| 6,355,070 B1 | 3/2002 | Andersen et al. | |
| 6,379,816 B1 | 4/2002 | De Loose et al. | |
| 6,403,241 B1 | 6/2002 | Chen et al. | |
| 6,425,924 B1 * | 7/2002 | Rousseau | A61B 17/0057 606/151 |
| 6,461,385 B1 | 10/2002 | Gayer et al. | |
| 6,497,728 B2 | 12/2002 | Yong | |
| 6,505,654 B1 | 1/2003 | Andersen et al. | |
| 6,524,344 B2 | 2/2003 | Yoon | |
| 6,544,472 B1 | 4/2003 | Compton et al. | |
| 6,592,617 B2 | 7/2003 | Thompson | |
| 6,685,990 B1 | 2/2004 | Zhong et al. | |
| 6,692,606 B1 | 2/2004 | Cederblad et al. | |
| 6,695,884 B1 | 2/2004 | Townley | |
| 6,716,514 B2 | 4/2004 | Nissing | |
| 6,723,120 B2 | 4/2004 | Yan | |
| 6,746,483 B1 | 6/2004 | Bojarski et al. | |
| 6,783,554 B2 * | 8/2004 | Amara | A61B 17/12168 606/151 |
| 6,805,966 B1 | 10/2004 | Formato et al. | |
| 6,827,743 B2 | 12/2004 | Eisermann et al. | |
| 7,052,513 B2 | 5/2006 | Thompson | |
| 7,189,263 B2 | 3/2007 | Erbe et al. | |
| 7,208,222 B2 * | 4/2007 | Rolfe | A61F 2/442 428/137 |
| 7,252,685 B2 | 8/2007 | Bindseil et al. | |
| 7,279,008 B2 | 10/2007 | Brown et al. | |
| 7,341,601 B2 | 3/2008 | Eisermann et al. | |
| 7,344,560 B2 | 3/2008 | Gregorich et al. | |
| 7,407,512 B2 | 8/2008 | Bojarski et al. | |
| 7,413,569 B2 * | 8/2008 | Sogaard-Andersen | A61F 2/0063 623/23.72 |
| 7,465,318 B2 | 12/2008 | Sennett et al. | |
| 7,527,644 B2 | 5/2009 | Mangiardi et al. | |
| 7,531,004 B2 | 5/2009 | Bagga et al. | |
| 7,534,451 B2 | 5/2009 | Erbe et al. | |
| 7,537,617 B2 * | 5/2009 | Bindsell | A61F 2/28 623/17.11 |
| 7,537,664 B2 | 5/2009 | O'Neill et al. | |
| 7,637,942 B2 | 12/2009 | Mangiardi et al. | |
| 7,655,047 B2 | 2/2010 | Swords | |

(56) References Cited

U.S. PATENT DOCUMENTS

| | | |
|---|---|---|
| 7,682,400 B2 | 3/2010 | Zwirkoski |
| 7,699,890 B2 | 4/2010 | Yan |
| 7,731,750 B2 | 6/2010 | Bojarski et al. |
| 7,740,657 B2 | 6/2010 | Brown, Jr. et al. |
| 7,749,264 B2 | 7/2010 | Gregorich et al. |
| 7,758,642 B2 | 7/2010 | Bojarski et al. |
| 7,824,433 B2 | 11/2010 | Williams |
| 7,828,802 B2 | 11/2010 | Levy et al. |
| 7,931,931 B2 | 4/2011 | Yan |
| 7,964,206 B2 | 6/2011 | Suokas et al. |
| 7,988,732 B2 | 8/2011 | Bojarski et al. |
| 8,007,529 B2 | 8/2011 | Yan |
| 8,029,506 B2 | 10/2011 | Levy et al. |
| 8,052,743 B2 | 11/2011 | Weber et al. |
| 8,100,973 B2 | 1/2012 | Sennett et al. |
| 8,142,886 B2 | 3/2012 | Noble et al. |
| 8,147,861 B2 | 4/2012 | Jones et al. |
| 8,172,897 B2 | 5/2012 | Gale et al. |
| 8,206,436 B2 | 6/2012 | Mangiardi et al. |
| 8,211,168 B2 | 7/2012 | Purdy et al. |
| 8,241,357 B2 | 8/2012 | Bhatnagar et al. |
| 8,247,333 B2 | 8/2012 | Sypeck et al. |
| 8,257,395 B2 | 9/2012 | Bhatnagar et al. |
| 8,268,099 B2 | 9/2012 | O'Neill et al. |
| 8,268,100 B2 | 9/2012 | O'Neill et al. |
| 8,287,915 B2 | 10/2012 | Clineff et al. |
| 8,329,091 B2 | 12/2012 | Maffia |
| 8,350,186 B2 * | 1/2013 | Jones .................. B22F 5/10 219/121.85 |
| 8,382,837 B2 | 2/2013 | Sennett et al. |
| 8,430,930 B2 | 4/2013 | Hunt |
| 8,454,705 B2 | 6/2013 | Pressacco et al. |
| 8,461,478 B2 | 6/2013 | Chen et al. |
| 8,532,806 B1 | 9/2013 | Masson |
| 8,551,173 B2 | 10/2013 | Lechmann et al. |
| 8,556,981 B2 | 10/2013 | Jones et al. |
| 8,679,166 B2 | 3/2014 | Bhatnagar et al. |
| 8,728,387 B2 | 5/2014 | Jones et al. |
| 8,734,520 B2 | 5/2014 | Zwirkoski |
| 8,764,809 B2 | 7/2014 | Lorenz et al. |
| 8,814,930 B2 | 8/2014 | Zheng et al. |
| 8,831,501 B2 | 9/2014 | Vella et al. |
| 8,888,862 B2 | 11/2014 | McDonnell et al. |
| 8,900,620 B2 | 12/2014 | Fulmer et al. |
| 8,906,022 B2 | 12/2014 | Krinke et al. |
| 8,932,366 B2 | 1/2015 | Shih |
| 8,956,394 B1 | 2/2015 | McDonnell |
| 8,986,767 B2 | 3/2015 | Batchelder |
| 8,992,537 B1 | 3/2015 | McDonnell |
| 8,992,619 B2 | 3/2015 | Patterson et al. |
| 8,992,703 B2 | 3/2015 | O'Neill et al. |
| 9,052,481 B2 | 6/2015 | Brunner et al. |
| 9,114,032 B1 | 8/2015 | Pulugurtha |
| 9,135,374 B2 * | 9/2015 | Jones .................. G06F 30/00 |
| D740,427 S | 10/2015 | McDonnell et al. |
| 9,155,819 B2 | 10/2015 | Fonte et al. |
| 9,180,010 B2 | 11/2015 | Dong et al. |
| 9,206,827 B2 | 12/2015 | Loree et al. |
| 9,232,971 B2 | 1/2016 | Sennett |
| 9,237,917 B2 | 1/2016 | Sennett et al. |
| 9,254,199 B2 | 2/2016 | Biedermann et al. |
| 9,265,601 B2 | 2/2016 | Bojarski et al. |
| 9,326,840 B2 * | 5/2016 | Mortarino .......... A61L 27/3604 |
| 9,408,651 B2 | 8/2016 | Sennett et al. |
| 9,415,137 B2 | 8/2016 | Meridew et al. |
| 9,421,108 B2 | 8/2016 | Hunt |
| 9,456,901 B2 | 10/2016 | Jones et al. |
| 9,526,539 B2 | 12/2016 | Zwirkoski |
| 9,526,544 B1 | 12/2016 | Kumar |
| 9,527,273 B2 | 12/2016 | Moors |
| 9,532,806 B2 | 1/2017 | McDonnell |
| 9,545,317 B2 | 1/2017 | Hunt |
| 9,642,727 B2 | 5/2017 | Verschueren et al. |
| 9,777,380 B2 | 10/2017 | MacDonald et al. |
| 9,833,955 B2 | 12/2017 | Muller et al. |
| 9,907,593 B2 | 3/2018 | McDonnell |
| 9,918,849 B2 | 3/2018 | Morris et al. |
| 9,943,351 B2 | 4/2018 | McDonnell et al. |
| 9,993,277 B2 | 6/2018 | Krinke et al. |
| 10,016,076 B2 | 7/2018 | Frazier |
| 10,029,422 B2 | 7/2018 | Meisner et al. |
| 10,070,975 B2 | 9/2018 | Dugan et al. |
| 10,092,404 B2 | 10/2018 | Hanssen et al. |
| 10,155,068 B2 * | 12/2018 | Seedhom .............. A61L 27/56 |
| 10,433,977 B2 | 10/2019 | Lechmann et al. |
| 10,517,658 B2 | 12/2019 | Cremer et al. |
| 10,888,362 B2 * | 1/2021 | Swarts ............. A61B 17/8085 |
| 2001/0013116 A1 | 8/2001 | Watanabe et al. |
| 2003/0109784 A1 | 6/2003 | Loh et al. |
| 2005/0070930 A1 * | 3/2005 | Kammerer .......... A61F 2/0063 606/151 |
| 2005/0119758 A1 | 6/2005 | Alexander et al. |
| 2005/0240261 A1 * | 10/2005 | Rakos ................. A61F 2/88 623/1.51 |
| 2005/0256582 A1 | 11/2005 | Ferree |
| 2005/0283229 A1 | 12/2005 | Dugan et al. |
| 2006/0147332 A1 | 7/2006 | Jones et al. |
| 2006/0166807 A1 | 7/2006 | Ylanen et al. |
| 2006/0276908 A1 * | 12/2006 | Sogaard-Andersen ............... A61F 2/0063 623/23.72 |
| 2007/0141111 A1 | 6/2007 | Suokas et al. |
| 2007/0142914 A1 * | 6/2007 | Jones ................ B29C 37/0082 623/14.13 |
| 2007/0219612 A1 * | 9/2007 | Andreas .......... A61B 17/12022 623/1.11 |
| 2007/0219613 A1 * | 9/2007 | Kao ...................... A61F 2/91 623/1.11 |
| 2007/0276489 A1 | 11/2007 | Bindseil et al. |
| 2008/0206297 A1 | 8/2008 | Roeder et al. |
| 2009/0022615 A1 | 1/2009 | Entezarian |
| 2009/0024147 A1 * | 1/2009 | Ralph .................. A61F 2/36 606/151 |
| 2009/0048675 A1 | 2/2009 | Bhatnagar et al. |
| 2009/0124147 A1 | 5/2009 | Pertez |
| 2009/0126225 A1 | 5/2009 | Jarvis |
| 2009/0192609 A1 | 7/2009 | Klabunde et al. |
| 2009/0312758 A1 | 12/2009 | Petit et al. |
| 2010/0070022 A1 | 3/2010 | Kuehling |
| 2010/0291401 A1 * | 11/2010 | Medina .................. B23K 26/32 219/121.66 |
| 2011/0008754 A1 | 1/2011 | Bassett et al. |
| 2011/0014081 A1 | 1/2011 | Jones et al. |
| 2011/0070358 A1 | 3/2011 | Mauch et al. |
| 2011/0152865 A1 | 6/2011 | Ralph et al. |
| 2011/0307053 A1 | 12/2011 | Gale et al. |
| 2012/0132631 A1 | 5/2012 | Wescott et al. |
| 2012/0232654 A1 | 9/2012 | Sharp et al. |
| 2013/0096371 A1 * | 4/2013 | Arcand .............. A61F 2/0063 600/37 |
| 2013/0171466 A1 | 7/2013 | Maffia |
| 2013/0218288 A1 * | 8/2013 | Fonte ................. A61F 2/3662 623/23.5 |
| 2013/0268085 A1 | 10/2013 | Dong et al. |
| 2013/0325126 A1 | 12/2013 | Bradica et al. |
| 2013/0325142 A1 | 12/2013 | Hunter et al. |
| 2014/0037873 A1 * | 2/2014 | Cheung .............. E04B 1/34384 428/34.1 |
| 2014/0128916 A1 | 5/2014 | Williams |
| 2014/0249643 A1 | 9/2014 | Jones et al. |
| 2014/0277150 A1 | 9/2014 | Jones et al. |
| 2014/0277569 A1 * | 9/2014 | Lange .............. A61B 17/7062 623/23.51 |
| 2014/0364935 A1 * | 12/2014 | Eli ...................... A61F 2/915 623/1.12 |
| 2015/0032197 A1 | 1/2015 | Bar et al. |
| 2015/0037601 A1 | 2/2015 | Blackmore |
| 2015/0045903 A1 | 2/2015 | Neal |
| 2015/0202047 A1 | 7/2015 | Patterson et al. |
| 2015/0224710 A1 | 8/2015 | El-Siblani |
| 2015/0230925 A1 | 8/2015 | Strippgen |
| 2015/0239046 A1 | 8/2015 | McMahan et al. |
| 2015/0258735 A1 | 9/2015 | O'Neill et al. |

(56) References Cited

U.S. PATENT DOCUMENTS

| | | |
|---|---|---|
| 2015/0265438 A1 | 9/2015 | Hossainy et al. |
| 2015/0282746 A1 | 10/2015 | Yousefi et al. |
| 2015/0282945 A1 | 10/2015 | Hunt |
| 2015/0374521 A1 | 12/2015 | Zheng et al. |
| 2016/0067375 A1 | 3/2016 | Holmes et al. |
| 2016/0116267 A1 | 4/2016 | McKendrick |
| 2016/0157904 A1 | 6/2016 | Zeetser et al. |
| 2016/0166302 A1 | 6/2016 | Tan-Malecki et al. |
| 2016/0167312 A1 | 6/2016 | Feinberg et al. |
| 2016/0175085 A1 | 6/2016 | Johnson et al. |
| 2016/0199201 A1* | 7/2016 | Weiss ............ A61F 2/78 219/76.1 |
| 2016/0199914 A1 | 7/2016 | Potter |
| 2016/0213403 A1 | 7/2016 | Bowden et al. |
| 2016/0228608 A1 | 8/2016 | Hakimi et al. |
| 2016/0287756 A1* | 10/2016 | Lewis ............ B33Y 10/00 |
| 2016/0338626 A1 | 11/2016 | Wang et al. |
| 2016/0340542 A1 | 11/2016 | Kim et al. |
| 2016/0375676 A1 | 12/2016 | Ritchie et al. |
| 2017/0064840 A1 | 3/2017 | Espalin et al. |
| 2017/0165790 A1 | 6/2017 | McCarthy et al. |
| 2017/0218228 A1 | 8/2017 | Jose et al. |
| 2018/0271572 A1* | 9/2018 | Whyne ............ A61F 2/2875 |
| 2018/0272607 A1 | 9/2018 | Chaffins et al. |
| 2018/0361510 A1 | 12/2018 | Stamp et al. |

FOREIGN PATENT DOCUMENTS

| | | | | |
|---|---|---|---|---|
| CA | 2615708 C | * | 4/2012 | ............ A61F 2/06 |
| CN | 108601659 A | * | 9/2018 | ............ A61F 2/2803 |
| CN | 110384573 A | * | 10/2019 | ............ A61F 2/32 |
| CN | 110612194 A | * | 12/2019 | ............ A61L 27/26 |
| DE | 2842847 A1 | | 4/1980 | |
| DE | 202004018209 U1 | | 1/2005 | |
| DE | 102006047663 A1 | | 4/2008 | |
| DE | 102006055432 A1 | * | 5/2008 | ......... A41D 31/0055 |
| EP | 0016480 A1 | | 10/1980 | |
| EP | 0526682 A1 | | 2/1993 | |
| EP | 1683593 A2 | | 7/2006 | |
| EP | 2606859 A1 | | 6/2013 | |
| KR | 101317706 B1 | * | 10/2013 | ............ A61F 2/0063 |
| WO | 03082550 A2 | | 10/2003 | |
| WO | 2004031086 A1 | | 4/2004 | |
| WO | 2012078955 A1 | | 6/2012 | |
| WO | 2013163398 A1 | | 10/2013 | |
| WO | 2015013479 A2 | | 1/2015 | |

OTHER PUBLICATIONS

Adam Cohen et al: "Microscale metal additive manufacturing of multi-component medical devices", Rapid Prototyping Journal, vol. 16, No. 3, Apr. 27, 2010 (Apr. 27, 2010), pp. 209-215, XP055704003, GB ISSN: 1355-2546, DOI: 10.1108/13552541011034889.

Wang et al: "A Unit Cell Approach for Lightweight Structure and Compliant Mechanism", Dissertation, Dec. 1, 2005 (Dec. 1, 2005), XP055671658, Retrieved from the Internet:URL https://pdfs.semanticscholar.org/f827/90e48d743feb2faf1d5da2a960cf1d9611c2.pdf [retrieved on Feb. 26, 2020].

Exeter™ Universal Hip System, Stryker Corporation; Admitted as Prior Art at least as of Dec. 20, 2013; 1 page.

McNichols Industrial Architectural Hole Products Solutions, downloaded from the internet: http://www.mcnichols.com/products/expanded/ on Nov. 12, 2013; 2 pages.

C.K. Chua et al. Development of a Tissue Engineering Scaffold Structure Library for Rapid Prototyping. Parts 1 and 2, International Journal of Advanced Manufacturing Technology, Feb. 2003, vol. 21, pp. 291-312.

Extended European Search Report for Application No. EP16204268.3 dated May 22, 2017.

Liu, "Degradable Scaffold Microstructure of Artificial Bioactive Bone fabricated by 3D Braiding Method", Applied Mechanics and Materials, vol. 610, pp. 980-983, Aug. 1, 2014.

Wang et al., "A Hybrid Geometric Modeling Method for Large Scale Conformal Cellular Structures," ASME Journal of Computing and Information Science in Engineering, 2006, 13 pages.

Deangelis, Stephen, "3D Printing and the Supply Chain", Supply Chain Brief, Enterra Solutions, Mar. 25, 2011, sourced from the web, https://www.enterrasolutions.com/blog/3d-printing-and-the-supply-chain/ on Jan. 7, 2019, 6 pages.

"The Printed World", The Economist, Feb. 10, 2011, acquired from the web, https://www.economist.com/briefing/2011/02/10/the-printed-world?story_id=18114221 on Jan. 7, 2019, 12 pages.

Partial European Search Report for EP18203809.1 dated Mar. 21, 2019.

Search report from Office Action dated Apr. 9, 2019 for Australian Application 2018204211.

* cited by examiner

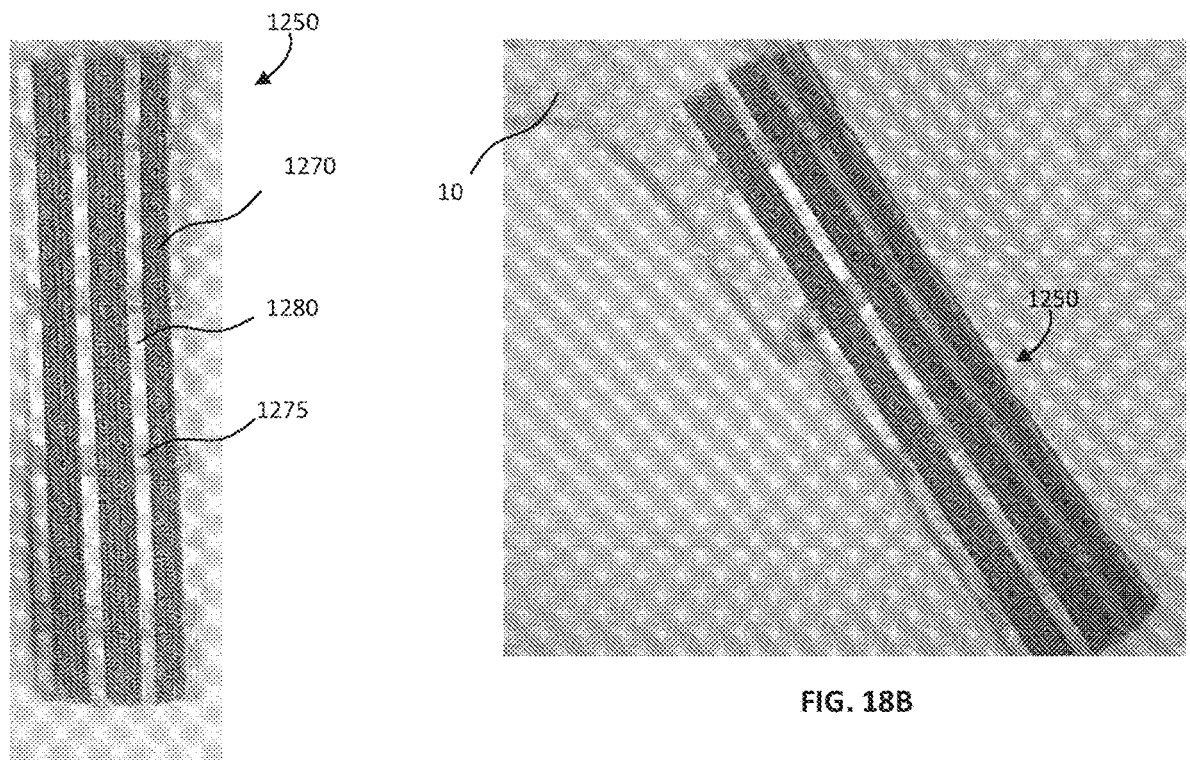
FIG. 18B
FIG. 18A
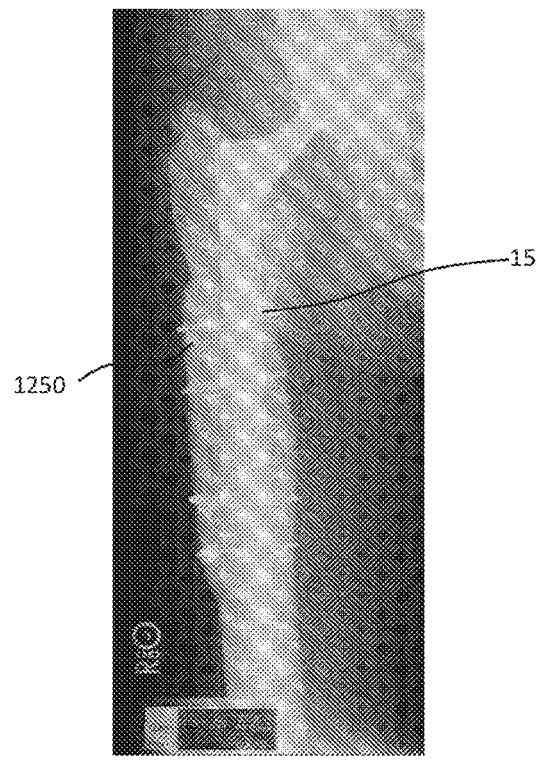
FIG. 18C

POROUS STRUCTURES PRODUCED BY ADDITIVE LAYER MANUFACTURING

CROSS-REFERENCE TO RELATED APPLICATION

The present application is a continuation of U.S. patent application Ser. No. 14/969,695, filed Dec. 15, 2015, the disclosure of which is incorporated herein by reference.

FIELD OF THE INVENTION

The present invention relates generally to preparing porous structures, and in particular to the preparation of mesh structures by way of additive manufacturing.

BACKGROUND OF THE INVENTION

The field of free-form fabrication has seen many important recent advances in the fabrication of articles directly from computer controlled databases. These advances, many of which are in the field of rapid manufacturing of articles such as prototype parts and mold dies, have greatly reduced the time and expense required to fabricate articles. This is in contrast to conventional machining processes in which a block of material, such as a metal, is machined according to engineering drawings.

Examples of modern rapid manufacturing technologies include additive layer manufacturing techniques such as electron beam melting, selective laser sintering (SLS), selective laser melting (SLM), and other three-dimensional (3-D) processes. When employing these technologies, articles are produced in layer-wise fashion from a laser-fusible powder that is dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. Detailed descriptions of the SLS technology may be found in U.S. Pat. Nos. 4,863,538, 5,017,753, 5,076,869, and 4,944,817, the entire disclosures of which are incorporated by reference herein. Similarly, a detailed description of the use of SLM technology may be found in U.S. Pat. No. 7,537,664 ("the '664 Patent"), the disclosure of which is incorporated by reference herein. The SLM and SLS technologies have enabled the direct manufacture of solid or porous three-dimensional articles of high resolution and dimensional accuracy from a variety of materials including wax, metal and metal alloys, metal powders with binders, polycarbonate, nylon, other plastics and composite materials, such as polymer-coated metals and ceramics.

Other non-powder based additive manufacturing technologies are also known to produce high resolution and dimensionally accurate articles. For example, in fused filament fabrication (FFF) or Plastic Jet Printing (PJP), strands of molten material are extruded from a nozzle to form layers onto a substrate in which the material hardens upon extrusion. Using digital light processing (DLP), photosensitive resin plastic is cured by light and built layer by layer from the bottom-up or a vat of liquid polymer is exposed to balanced levels of ultraviolet light and oxygen to produce a part often from the top-down. In inkjet 3D printing, a liquid binding material is selectively deposited across a thin layer of a powder and the process is repeated in which each new layer is adhered to the previous layer.

The invention claimed in the '664 Patent is one of several commonly owned by Howmedica Osteonics Corporation that relate to the additive manufacturing area. For instance, U.S. Pat. Appl. Publ. Nos. 2006/0147332 A1 ("the '332 Publication") U.S. Pat. Appl. Publ. No. 2011/0014081 A1 ("the '081 Publication"), U.S. Pat. No. 8,992,703 ("the '703 Patent"), U.S. Pat. No. 9,135,374 ("the '374 Patent"), and U.S. Pat. No. 9,180,010 ("the '010 Patent"), the entire disclosures of which are hereby incorporated by reference herein, have taught the generation and organization of a population of porous geometry, a mathematical representation of the portion of geometry of the porous structure to be built within a region defined by a predetermined unit cell or imaginary volume, to fill and form a predetermined build geometry, i.e., a model build structure, which may be used to produce a near net-shape of an intended porous tissue in-growth structure. The predetermined build geometry, or overall computer-aided design (CAD) geometry, may refer to the mathematical or pictorial representation (such as that on a computer display) of the intended physical structure to be manufactured. In the case of physical components that include both porous material and solid material, the predetermined build geometry may be an assembly of solid and porous CAD volumes that define the outer boundaries of the respective solid and porous materials intended to be manufactured. Furthermore, these applications teach the randomization of the position of interconnected nodes, or points of intersection between two struts or between a strut and a substrate, that define each of the porous geometries while maintaining the interconnectivity between the nodes. As further taught in these applications, such randomization may be accomplished by changing the coordinate positions of the nodes, in the x, y, and z directions of a Cartesian coordinate system, to new positions based on a defined mathematical function.

During surgical operations on one or more bones, orthopedic implants are generally adhered to a bony surface by bone cement. Even proper preparation of delivery of bone cement to a smooth bony surface can result in aseptic loosening of the implant and cement over time, especially when filling large void spaces such as in the proximal tibia and distal femur, requiring a revision surgery to be performed. Current implants, which typically require the use of biocompatible materials such as titanium, used to retain bone cement lack flexibility and are difficult to shape for a proper fit in a non-uniform space. Such implants are non-porous and thus lack limited surface area for contact with bone. Implants produced using additive layer manufacturing techniques have been built with strong scaffolds, but such implants are too rigid to allow for adequate deformation to fill void spaces created by bone degradation.

Thus, a new method is needed to create flexible structures which still provide mechanical strength to resist tensile and compressive forces, especially impact forces applied to bone and orthopedic implants.

BRIEF SUMMARY OF THE INVENTION

In accordance with an aspect, a three-dimensional structure may be formed. In forming the three-dimensional structure, a first layer of a material may be deposited onto a substrate. A first layer of the material may be scanned with a high energy beam to at least partially melt the first layer of the material. Successive layers of the material may be deposited onto the first layer. Each of the successive layers of the material may be scanned with the high energy beam at predetermined locations to form at least a first segment overlapping a second segment and underlapping a third segment.

In some arrangements, any of the segments may be a curvilinear segment. In some arrangements, any of the segments may be a rectilinear segment. In some arrangements, any of the segments may include both curvilinear and rectilinear portions.

In some arrangements, the three-dimensional structure may be in the form of a mesh defined by a weave pattern or a chain-link pattern.

In some arrangements, the material may be any of titanium, a titanium alloy, stainless steel, magnesium, a magnesium alloy, cobalt, a cobalt alloy, a cobalt chrome alloy, nickel, a nickel alloy, tantalum, and niobium, polyethylene (PE) and variations thereof, polyetheretherketone (PEEK), polyetherketone (PEK), acrylonitrile butadiene styrene (ABS), silicone, and cross-linked polymers, bioabsorbable glass, ceramics, and biological active materials including collagen/cell matrices.

In some arrangements, when scanning each of the successive layers at predetermined locations a fourth segment spaced from the first segment, underlapping the second segment, and overlapping the third segment may be formed.

In some arrangements, the second and third segments may be spaced from each other.

In some arrangements, the third segment may be the second segment such that the first segment underlaps and overlaps the second segment. In such arrangements, the second and third segments may form part of a link, which may form a portion of a chain mail structure.

In some arrangements, the first segment may completely surround the second segment. In such arrangements, the first segment may be a link of a chain mail structure.

In some arrangements, the second segment may completely surround the first segment. In such arrangements, the second segment may be a link of a chain mail structure.

In some arrangements, when scanning each of the successive layers at predetermined locations a plurality of segments may be formed that may completely surround the first segment.

In some arrangements, a first additional layer of the material may be deposited onto at least a predetermined location of the first segment. In some such arrangements, the first additional layer of the material may be scanned with the high energy beam at the predetermined location of the first segment. In this manner, the first additional layer of the material may be fused to the first segment at the predetermined location.

In some arrangements, successive additional layers of the material may be deposited onto the first additional layer. In some such arrangements, each of the successive additional layers may be scanned with the high energy beam at predetermined locations. In this manner, at least a first additional segment may be formed overlapping a second additional segment and underlapping a third additional segment in which the first additional segment may be fused to at least the first segment at the predetermined location of the first segment.

In some arrangements, the third additional segment may be the second additional segment such that the first additional segment underlaps and overlaps the second additional segment. In such arrangements, the second and third segments may form part of a link, which may form a portion of a chain mail structure.

In some arrangements, when scanning each of the successive additional layers at predetermined locations, a fourth additional segment spaced from the first additional segment, underlapping the second additional segment, and overlapping the third additional segment may be formed.

In some arrangements, when depositing the first additional layer of the material, the first additional layer of the material may be further deposited onto predetermined locations of the second, third, and fourth segments. In some such arrangements, when scanning the first additional layer of the material with the high energy beam, the first additional layer may be fused to each of the second, third, and fourth segments at the respective predetermined locations of the second, third, and fourth segments.

In some arrangements, successive additional layers of the material may be deposited onto the first additional layer. In some such arrangements in which successive additional layers of the material may be deposited onto the first additional layer, each of the successive additional layers may be scanned with the high energy beam at predetermined locations to form at least one symbol. In some such arrangements forming at least one symbol, any of such symbols may be fused to at least the first segment at the predetermined location of the first segment. In some such arrangements forming at least one symbol, any of such symbols may be an alphanumeric character.

In some arrangements, when scanning each of the successive layers at predetermined locations, at least one barb may be formed. Any such barbs may extend from any of the first, second, and third segments.

In some arrangements, when scanning each of the successive layers at predetermined locations, a first series of segments extending in a first direction and a second series of segments extending in a second direction transverse to the first direction may be formed. The first series of segments may include the first segment. The second series of segments may include the second and third segments. Some or all of the segments of the first series of segments may overlap a plurality of segments of the second series of segments and may underlap another plurality of segments of the second series of segments such that the first and second series of segments form a first mesh.

In some arrangements, the first mesh may be a flexible sheet. The first mesh may be foldable such that a substantially planar first portion of the first mesh lies in a plane at an angle of up to substantially 180 degrees to a plane in which a substantially planar second portion of the first mesh lies.

In some arrangements, the first mesh may be a flexible sheet formed in the shape of a cone or a frustum of a cone.

In some arrangements, the first mesh may define a pocket. The pocket of the first mesh may be stamped to form a cavity in the pocket. In some such arrangements, when the first mesh is stamped by a tool, a bottom surface of the cavity of the first mesh may conform to a bottom surface of the tool. When the first mesh is stamped by a tool having protrusions extending from a flat base, a bottom surface of the first mesh may have corresponding protrusions extending from the bottom surface upon being stamped by the tool.

In some arrangements, when scanning each of the successive layers of the material at predetermined locations, a third series of segments extending in a third direction and a fourth series of segments extending in a fourth direction transverse to the third direction may be formed. In some such arrangements, each of the segments of the third series of segments may overlap a plurality of segments of the fourth series of segments and may underlap a plurality of segments of the fourth series of segments. In this manner, the third and fourth series of segments may form a second mesh. In some such arrangements, when scanning each of the successive layers at predetermined locations, at least one segment may be formed that underlaps and overlaps at least one segment of the first and second series of segments and at least one segment of the third and fourth segments such that the first and second meshes may be rotatably attached to each other.

In some arrangements, the first and the third directions are the same. In the same or in other arrangements, the second and the fourth directions are the same.

In some arrangements, any of the first and the second meshes may have a profile substantially in the form of any of a square, a rectangle, a circle, and a triangle.

In some arrangements, the first and the second meshes may have edges adjacent and substantially parallel to each other such that upon rotation of either of the edges about the other edge, the edges do not interfere with such rotation.

In some arrangements, pluralities of the segments of the first and second series of segments may define a bore through a thickness of the scanned successive layers of the material.

In some arrangements, when scanning each of the successive layers at predetermined locations an outer ring, and wherein ends of pluralities of the segments of the first and second series of segments are fused to an outer perimeter of the outer ring, an inner perimeter opposite the outer perimeter of the outer ring defining the bore through the thickness of the scanned successive layers of the material.

In some arrangements, when scanning each of the successive layers at predetermined locations, an inner ring concentric with the outer ring may be formed. In some such arrangements when scanning each of the successive layers at predetermined locations, segments fused to and between the inner perimeter of the outer ring and an outer perimeter opposite an inner perimeter of the inner ring may be formed. In such arrangements, the inner perimeter of the inner ring may define the bore through the thickness of the scanned successive layers of the material.

In some arrangements, when scanning each of the successive layers at predetermined locations a stud or rivet may be formed. In some such arrangements, ends of pluralities of the segments of the first and second series of segments may fused to the perimeter of the stud or rivet.

In some arrangements, when scanning each of the successive layers at predetermined locations, a third series of segments extending in a third direction and a fourth series of segments extending in a fourth direction transverse to the third direction may be formed. In some such arrangements, each of the segments of the third series of segments may overlap a plurality of segments of the fourth series of segments and may underlap a plurality of segments of the fourth series of segments. In this manner, the third and fourth series of segments may form a second mesh. In some such arrangements, when scanning each of the successive layers at predetermined locations, a solid section may be formed. The solid section may be fused to each of the first and second meshes. In this manner, the solid section may be movable relative to portions of each of the first and second meshes.

In some arrangements, when scanning each of the successive layers at predetermined locations a hook extending from the first segment may be formed.

In some arrangements, the first segment may be fused to at least one of the second and the third segments.

In some arrangements, the first segment may be fused to only one of the second and the third segments.

In accordance with another aspect, bone ingrowth may be facilitated. In facilitating such bone ingrowth, a porous tissue ingrowth structure may be formed in the shape of a mesh implant. In forming the mesh implant, a first layer of a material may be deposited onto a substrate. A first layer of the material may be scanned with a high energy beam to at least partially melt the first layer of the material. Successive layers of the material may be deposited onto the first layer. Each of the successive layers of the material may be scanned with the high energy beam at predetermined locations to form at least a first segment overlapping a second segment and underlapping a third segment. The mesh implant may be shaped into a desired shape. The mesh implant may have a porosity to promote bone ingrowth. The mesh implant may be placed against a bone portion. A bone implant may be placed against bone cement such that the bone cement contacts both the mesh implant and the bone implant. The mesh implant may prevent contact of the bone cement with bone ingrown into the mesh implant.

In accordance with another aspect, a three-dimensional structure may be formed. In forming the three-dimensional structure, a first layer of a material may be formed over at least a substrate. The first layer of the material may be scanned with a high energy beam to form a first pattern. The first pattern may include a first portion (a1) of a first solid portion (A). A second layer of the material may be deposited over the first layer of the material. The second layer of the material may be scanned with a high energy beam to form a second pattern. The second pattern may include a first portion (b1) of a second solid portion (B). A third layer of the material may be deposited over at least a substrate. The third layer of the material may be scanned with a high energy beam to form a third pattern. The third pattern may include a second portion (a2) of the first solid portion (A). A fourth layer of the material may be deposited over at least the second layer of the material. The fourth layer of the material may be scanned with a high energy beam to form a fourth pattern. The fourth pattern may include a third portion (a3) of the first solid portion (A). A fifth layer of the material may be deposited over at least the third layer of the material. The fifth layer of the material may be scanned with a high energy beam to form a fifth pattern. The fifth pattern may include a first portion (c1) of a third solid portion (C). A sixth layer of the material may be deposited over at least the fifth layer of the material. The sixth layer of the material may be scanned with a high energy beam to form a sixth pattern. The sixth pattern may include a fourth portion (a4) of the first solid portion (A). The first, second, third, and fourth portions of the first solid portion (A) may be attached to each other such that the first solid portion (A) at least partially wraps around the second solid portion (B) and the third solid portion (C). An example of a model used to form such a three-dimensional structure is shown in FIG. 4A in which examples of first, second, third, and fourth portions, and first, second, and third solid portions are labeled accordingly.

In some arrangements, at least some of the second, third, fourth, and fifth layers may be the same layer.

In some arrangements, the second solid portion (B) is the same as the third solid portion (C) such that the first solid portion (A) forms a link.

In some arrangements, the first and third layers may be the same layer such that the third pattern is part of the first pattern. In such arrangements, the first pattern may further include a first portion (d1) and a second portion (d2) of a fourth solid portion (D). The first portion (d1) and the second portion (d2) of the fourth solid portion (D) may be offset from the first portion (a1) and the second portion (a2) of the first solid portion (A) within the first pattern. In such arrangements, the second and fifth layers may be the same layer such that the fifth pattern is part of the second pattern. In such arrangements, the first portion (b1) of the second solid portion (B) and the first portion (c1) of the third solid portion (C) may be offset from each other. In such arrangements, the fourth and sixth layers may be the same layer such that the sixth pattern is part of the fourth pattern. In such arrangements, the fourth pattern may further include a third portion (d3) and a fourth portion (d4) of the fourth solid portion (D). In such arrangements, the third portion (d3) and the fourth portion (d4) of the fourth solid portion (D) may be offset from the third portion (a3) and the fourth portion (a4) of the first solid portion (A) within the fourth pattern. In such arrangements, the first, second, third, and fourth portions of the fourth solid portion (D) may be attached to each other such that the fourth solid portion (A) weaves around the second solid portion (B) and the third solid portion (C) in the opposite manner that the first solid portion weaves around the second solid portion (B) and the third solid portion (C).

In some arrangements, at least one of the second portion (a2) and the third portion (a3) of the first solid portion (A) may be fused to at least one of the first portion (b1) of the second solid portion (B) and the first portion (c1) of the third solid portion (C).

In accordance with another aspect, a non-transitory computer-readable storage medium may have computer readable instructions of a program stored on the medium. The instructions, when executed by a processor, cause the processor to perform a process of preparing a computer-generated model of a three-dimensional structure constructed of unit cells. In performing the process, a computer-generated component file may be prepared. The computer-generated component file may include a porous CAD volume which may have a boundary. A space may be populated, by a processor, to include the porous CAD volume. The porous CAD volume may be populated with unit cells. Each of the unit cells may be populated, by a processor, with at least one segment geometry to form a plurality of segment geometries. A first segment geometry of the plurality of segment geometries may overlap a second segment geometry of the plurality of segment geometries and underlap a third segment geometry of the plurality of segment geometries.

BRIEF DESCRIPTION OF THE DRAWINGS

FIGS. 18A-18C are views of an application of mesh sheets in accordance with embodiment;

DETAILED DESCRIPTION

This invention relates generally to generating computer models of three-dimensional structures. These models may be used to prepare porous tissue in-growth structures in medical implants and prostheses. The models may include features corresponding to tangible structures.

Figure 1:
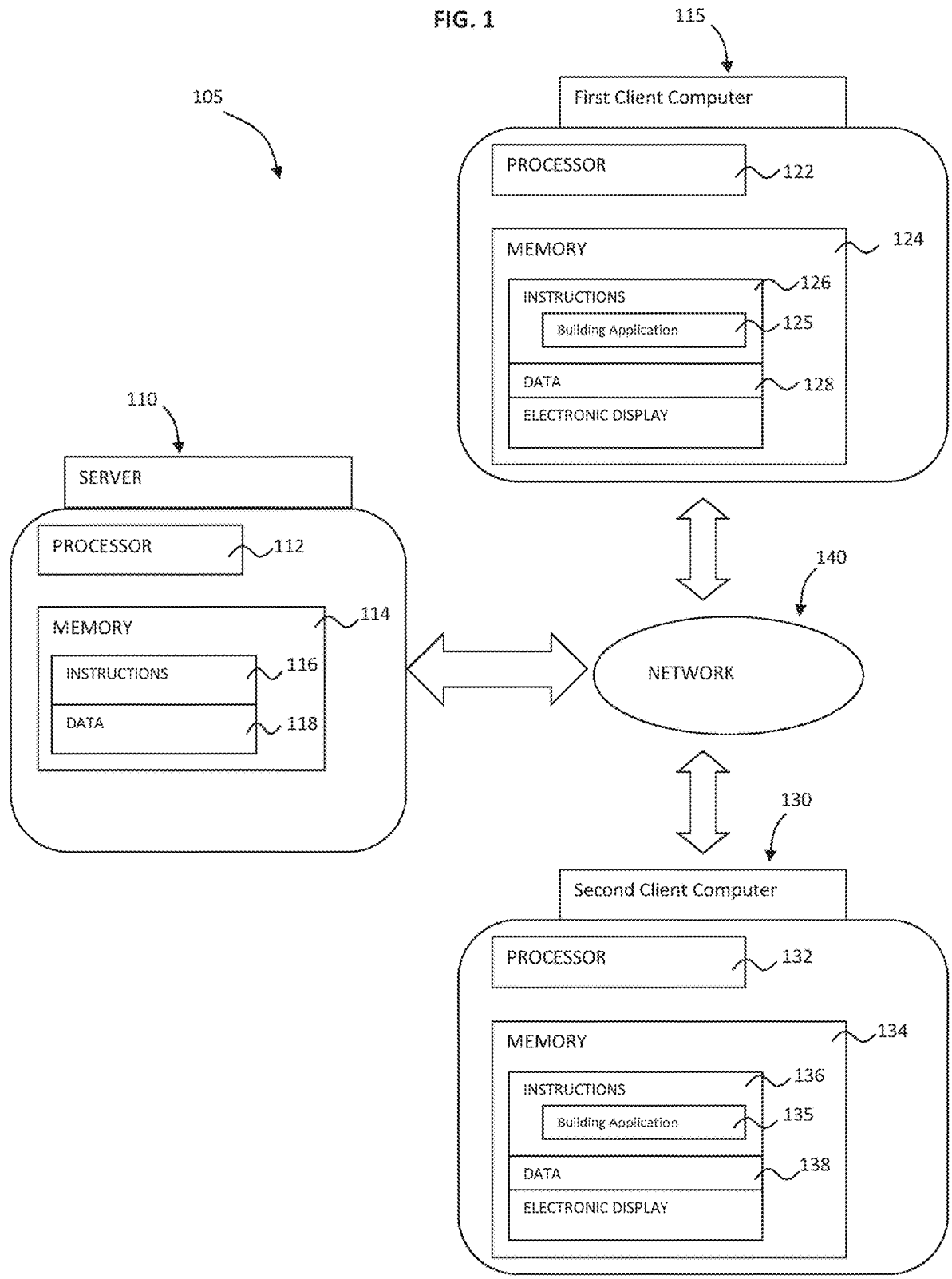
FIG. 1 is a functional diagram of a system in accordance with an embodiment.

FIG. 1 depicts system 105 that may be used, among other functions, to generate, store and share three-dimensional models of structures. System 105 may include at least one server computer 110, first client computer 115, and in some instances, at least second client computer 130. These computers may send and receive information via network 140. For example, a first user may generate a model at first client device 115. The model may then be uploaded to server 110 and distributed via network 140 to second client computer 130 for viewing and modification by a second user, who or which may be the first user.

Network 140, and intervening communication points, may comprise various configurations and protocols including the Internet, World Wide Web, intranets, virtual private networks, wide area networks, local networks, private networks using communication protocols proprietary to one or more companies, Ethernet, WiFi and HTTP, and various combinations of the foregoing. Such communication may be facilitated by any device capable of transmitting data to and from other computers, such as modems (e.g., dial-up, cable or fiber optic) and wireless interfaces. Although only a few devices are depicted in FIG. 1, a system may include a large number of connected computers, with each different computer being at a different communication point of the network.

Each of computers 110, 115, and 130 may include a processor and memory. For example, server 110 may include memory 114 which stores information accessible by processor 112, computer 115 may include memory 124 which stores information accessible by processor 122, and computer 130 may include memory 134 which stores information accessible by processor 132.

Each of processors 112, 122, 132 may be any conventional processor, such as commercially available CPUs. Alternatively, the processors may be dedicated controllers such as an ASIC, FPGA, or other hardware-based processor. Although shown in FIG. 1 as being within the same block, the processor and memory may actually comprise multiple processors and memories that may or may not be stored within the same physical housing. For example, memories may be a hard drive or other storage media located in a server farm of a network data center. Accordingly, references to a processor, memory, or computer will be understood to include references to a collection of processors, memories, or computers that may or may not operate in parallel.

The memories may include first part storing applications or instructions 116, 126, 136 that may be executed by the respective processor. Instructions 116, 126, 136 may be any set of instructions to be executed directly (such as machine code) or indirectly (such as scripts) by the processor. In that regard, the terms "applications," "instructions," "steps" and "programs" may be used interchangeably herein.

The memories may also include second part storing data 118, 128, 138 that may be retrieved, stored or modified in accordance with the respective instructions. The memory may include any type capable of storing information accessible by the processor, such as a hard-drive, memory card, ROM, RAM, DVD, CD-ROM, write-capable, and read-only memories or various combinations of the foregoing, where applications 116 and data 118 are stored on the same or different types of media.

In addition to a processor, memory and instructions, client computers 115 and may have all of the components used in connection with a personal computer. For example, the client computers may include electronic display (e.g., a monitor having a screen, a touch-screen, a projector, a television, a computer printer or any other electrical device that is operable to display information), one or more user inputs (e.g., a mouse, keyboard, touch screen and/or microphone), speakers, and all of the components used for connecting these elements to one another.

Instructions 126, 136 of the first and second client devices 115, 130 may include building applications 125, 135. For example, the building applications may be used by a user to create three-dimensional structures, such as those described further herein. The building applications may be associated with a graphical user interface for displaying on a client device in order to allow the user to utilize the functions of the building applications.

A building application may be a computer-aided design (CAD) 3-D modeling program or equivalent as known in the art. Available CAD programs capable of generating such a structure include Autodesk® AutoCAD®, Creo® by Parametric Technology Corporation (formerly Pro/Engineer), Siemens PLM Software NX™ (formerly Unigraphics NX), SOLIDWORKS® by SolidWorks Corporation, and CATIA® by Dassault Systemes. Such structures may be those described in the '421 Application.

Data 118, 128, 138 need not be limited by any particular data structure. For example, the data may be stored in computer registers, in a relational database as a table having a plurality of different fields and records, or XML documents. The data may also be formatted into any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data. For example, data 128 of first client device 115 may include information used by building application 125 to create three-dimensional models.

In addition to the operations described above and illustrated in the figures, various other operations will now be described. It should be understood that the following operations do not have to be performed in the precise order described below. Rather, various steps may be handled in a different order or simultaneously. Steps may also be omitted or added unless otherwise stated herein.

An overall three-dimensional representation of a component may first be generated by preparing a CAD model. This overall CAD model may be comprised of one or more distinct CAD volumes that are intended to be manufactured as either solid or porous physical structures, i.e., constructs.

Solid CAD volumes, which correspond to manufactured solid physical structures, can be sliced into layers of a predetermined thickness ready for hatching, re-merging with the porous volume (post-lattice generation), and subsequent manufacture.

Figure 2:
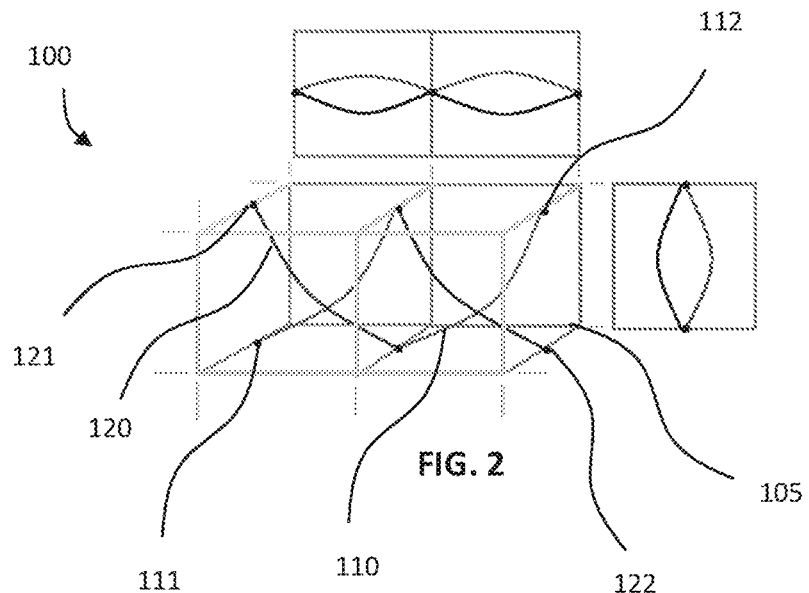
FIGS. 2-4B are various views of three-dimensional model representations of unit cells having wireframes located therein in accordance with other embodiments.

Porous CAD volumes, such as porous CAD volume 100 shown in the example of FIG. 2 and which correspond to manufactured porous geometries, can be processed using bespoke software. As in the example of FIG. 2, a porous geometry is made up of one or more segments 110, 120 organized within tessellated unit cells 105. Many designs are possible for a porous geometry which allows the porous geometry to impart various strength, surface, and/or other characteristics into the porous CAD volume. For example, porous geometries can be used to control the shape, type, degree, density, and size of porosity within the structure. Such porous geometry shapes can be dodecahedral, octahedral, tetrahedral (diamond), as well as other various shapes.

As further shown in FIG. 2, porous CAD volume 100 is formed by a plurality of unit cells 105 which each contain curvilinear segment geometry 110 and curvilinear segment geometry 120. Curvilinear segment geometry 110 within each unit cell 105 extend from an end 111 thereof located at a center of a lower left edge of the unit cell to an end 112 thereof located at a center of an upper right edge of the unit cell, and curvilinear segment geometries 120 within each unit cell 105 extend from an end 121 thereof located at a center of an upper left edge of the unit cell to an end 122 thereof located at a center of a lower right edge of the unit cell.

Unit cells 105 are adjacent to each other such that end 112 of curvilinear segment geometry 110 within one unit cell 105 abuts, and indeed is the same as, end 121 of curvilinear segment geometry 120 within adjacent unit cell 105 and such that end 122 of curvilinear segment geometry 120 within one unit cell 105 abuts, and is the same as, end 111 of curvilinear segment geometry 110 within adjacent unit cell 105. As shown, curvilinear segment geometry 110 within each unit cell 105 curves around curvilinear segment geometry 120 within the same unit cell. In this manner, a connected pair of curvilinear segment geometry 110 and curvilinear segment geometry 120 within adjacent unit cells 105 overlaps the other connected pair of curvilinear segment geometry 110 and curvilinear segment geometry 120 within the same adjacent unit cells.

Figure 3:
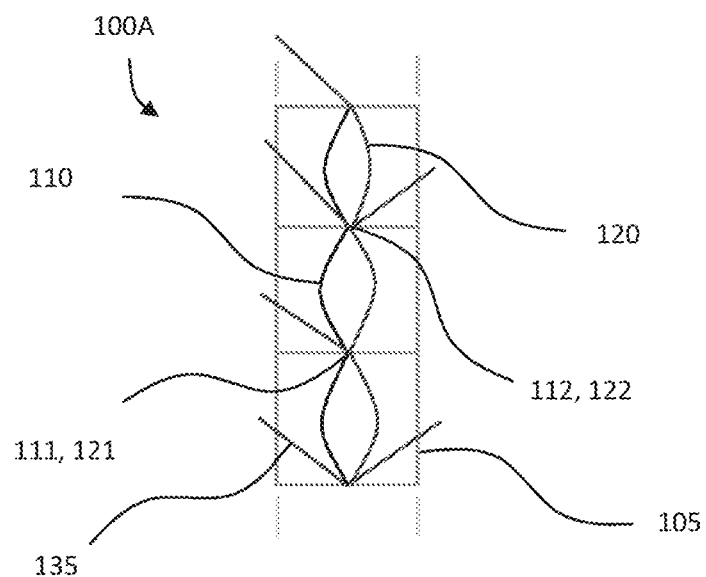

As shown in FIG. 3, porous CAD volume 100A includes unit cells 105 formed adjacent to other unit cells 105 such that ends of curvilinear segment geometries 110, 120 of one unit cell abut an end of the other curvilinear segment geometry of respective curvilinear segment geometries 110, 120 of the adjacent unit cell. As further shown, a plurality of barb geometries 135 extend from various ends 111, 112 of curvilinear segment geometries 110 and ends 121, 122 of curvilinear segment geometries 120 such that barb geometries 135 extend transversely across the curvilinear segment geometries 110, 120 corresponding to the respective ends. In this manner, a plurality of unit cells 105 may be tessellated to form the porous CAD volume 100A.

When used for medical implants, barb geometries, such as barb geometries 135, may correspond to physical barbs that encourage directional fixation of the implants. In such applications, the barbs may vary in spacing and length. Such barbs may be but are not limited to being on the order of 0.6-1.2 mm in length. Any directional barb hairs, branches, rods, and beads may also be incorporated into a porous mesh structure to encourage directional fixation with bone. As barb geometries, such as barb geometries 135, may be placed at any predetermined or, conversely, at randomly selected positions along segment geometries of a porous CAD volume, barbs corresponding to the barb geometries may be placed at any such corresponding positions on segments corresponding to segment geometries.

Figure 4A:
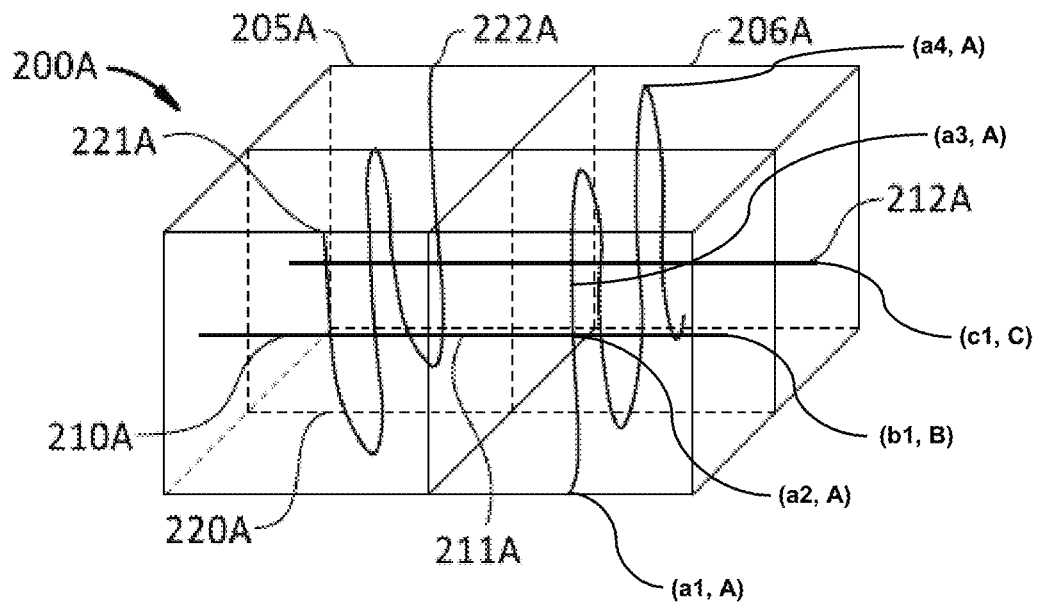

Referring now to FIG. 4A, porous CAD volume 200A formed by tessellation of a plurality of unit cells 205A, 206A each containing linear segment geometry 210A and curvilinear segment geometry 220A. As in this example, opposing ends 211A, 212A of linear segment geometry 210A within each unit cell 205A, 206A may extend from centers of opposite faces of the unit cell, and curvilinear segment geometry 220A of each unit cell 205A may extend from an end 221A thereof located at a center of an upper front edge of the unit cell, around the linear segment geometry, and to an end 222A thereof located at a center of an upper rear edge of the unit cell. In this manner, segment geometries 210A, 220A form portions of mesh geometry.

A plurality of unit cells 205A and separately a plurality of unit cells 206A may be adjacent to each other such that end 221A of curvilinear segment geometry 210A of one unit cell 205A, 206A abuts end 222A of curvilinear segment geometry 220A of respective adjacent unit cell 205A, 206A. As further shown, the plurality of unit cells 206A may be inverted relative to the plurality of unit cells 205A, and end 211A of linear segment geometry 210A of one unit cell 205A may abut end 212A of linear segment geometry 210A of respective adjacent unit cell 206A. In this manner, curvilinear segment geometries 210A of each of the plurality of unit cells 205A, 206A and the linear geometries 210A of each of the plurality of unit cells 205A, 206A may collectively form a woven mesh geometry. As in the example shown, the linear segment geometries 210A of the plurality of unit cells 205A, 206A may all be parallel to each other.

Figure 4B:
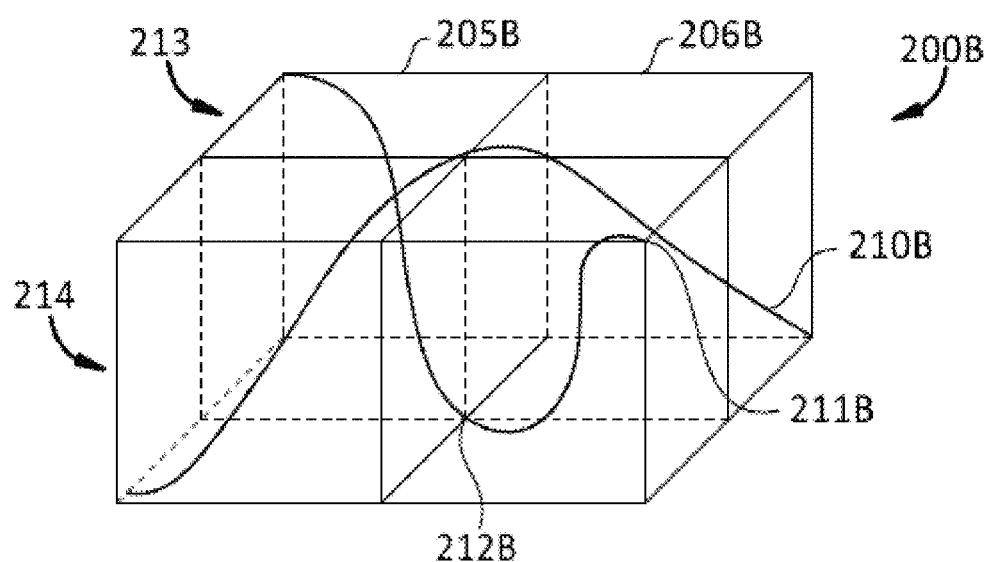

Referring to FIG. 4B, porous CAD volume 200B is formed by tessellation of a plurality of unit cells 205B, 206B each containing curvilinear segment geometry 210B in which curvilinear segment geometry 210B of unit cell 206B is inverted relative to curvilinear segment geometry 210B of unit cell 205B. As in this example, opposing ends 211B, 212B of curvilinear segment geometry 210B of each unit cell 205B, 206B may extend from opposite corners of the respective unit cells. Unit cells 205B may be diagonal from each other such that they share only one common edge, and similarly, unit cells 206B may be diagonal from each other such that they share only one common edge. In this manner, ends 212B of curvilinear segment geometries 210B of each of a first set of unit cells 205B, 206B may abut ends 211B of curvilinear segment geometries 210B of each of a second set of unit cells 205B, 206B located diagonally to the first set of the unit cells. In this manner, a connected pair of curvilinear segment geometry 210B of diagonally located set of unit cells 205B overlaps a connected pair of curvilinear segment geometry 210B of diagonally located set of unit cells 206B to form mesh geometry. As shown, such mesh geometry may be in the form of a woven mesh.

A larger mesh geometry may be formed by adding further sets of the four unit cells 205B, 206B to each of the four sets of two side faces 213, 214 of adjoining unit cells 205B, 206B, i.e., to the side faces 213, 214 around the circumference of the four-cubes shown in the illustration of FIG. 4B. In alternative arrangements, the mesh geometry defined by the four curvilinear segments 210B of the four unit cells 205B, 206B shown in FIG. 4B may be arranged in a single unit cell, which may be tessellated to form a porous CAD volume.

Other variations of unit cells 105 and 205, 206 in which at least one segment geometry defining the unit cell is curved or includes angled portions, which may be in the shape of a "V," "W" or other combination of linear portions, such that the segment geometry curves or wraps around another segment geometry of the unit cell are within the scope of the present technology. Such variations could also be used to form porous CAD volumes. In other arrangements, a CAD model may be generated without forming unit cells and thus without tessellation of features within the unit cells. Such CAD models created without tessellated unit cells may be in the form of a woven mesh, i.e., cross-hatch, geometry with overlapping and underlapping strips, i.e., ribbons. In some alternative arrangements, woven mesh geometries may have a plurality of adjacent segment geometries or set of segment geometries that overlap and underlap the same transverse corresponding segment geometries or set of segment geometries, e.g., in the form of a "double weave." In other variations of forming mesh geometries, the ends of the segment may be at any location within a unit cell so long as the segment geometries of each unit cell, alone or in combination with segment geometries of adjacent unit cells overlap and underlap segment geometries within the same unit cell or within adjacent unit cells, i.e., in a manner similar to the overlapping and underlapping of the segment geometries shown in FIGS. 4A and 4B. For example, ends may be but are not limited to being at corners of unit cells, centers of edges of unit cells, and the centers of faces of unit cells. In some arrangements, a percentage of the junctions where segment geometries of a porous CAD volume overlap each other may be fused together.

When fusion of such junctions is unevenly distributed, anisotropy in a physical mesh structure corresponding to a porous CAD volume may be created.

Figure 5:
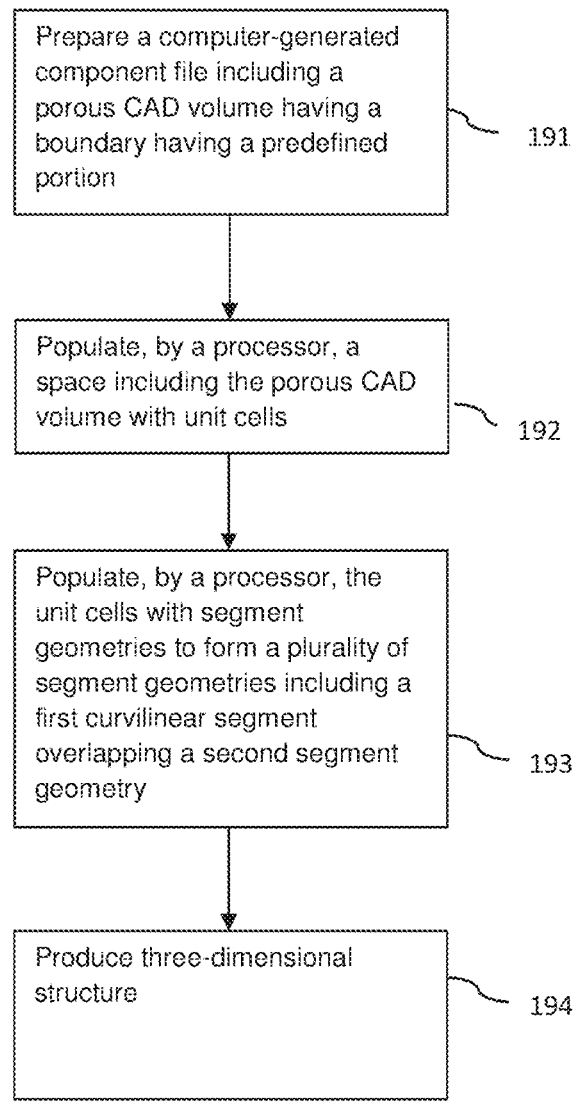
FIG. 5 is a process flow diagram in accordance with another embodiment.

Referring to FIG. 5, in an example of preparing a porous CAD volume of segment geometries, a computer-generated component file is prepared at a block 191. The component file includes a porous CAD volume with a boundary having at least one predefined portion. At a block 192, a space that includes the porous CAD volume is populated, by a processor, with unit cells. Such a space may be defined by sets of coordinates, such as Cartesian, polar, or spherical coordinates. At a block 193, the unit cells are populated with one or more segment geometries to form a plurality of segment geometries. As further shown at block 193, a first curvilinear segment geometry of the plurality of segment geometries overlaps a second segment geometry of the plurality of segment geometries and underlaps a third segment geometry of the plurality of segment geometries. In this manner, a computer-generated model of a three-dimensional structure constructed of segment geometries is prepared.

The above-described model geometries can be visualized in a number of ways, including but not limited to by voxelating the sliced output files from bespoke software that is being applied in an additive layer manufacturing machine. Utilizing developed algorithms and the output files, the data may be fed into a commercial software package, e.g., MATLAB® by MathWorks, Inc., and the images produced can be interpreted. At an optional block 194, a tangible three-dimensional structure having a shape corresponding to the computer-generated model may be produced. The shape of the three-dimensional structure may be in the form of a mesh structure, such as a mesh implant.

The approaches for generating the three-dimensional models described herein may be used for building various tangible structures and surfaces, specifically structures and surfaces for medical implants. Upon completion of a CAD model including the porous geometries and any solid geometries that may be connected to the porous geometries, an intended physical structure may be formed directly onto a substrate using a layered additive manufacturing process, including but not limited to electron beam melting (EBM), selective laser sintering (SLS), selective laser melting (SLM), and blown powder fusion for use with metal powders. Techniques such as but not limited to SLS, three-dimensional inkjet printing (3DP), stereolithography (SLA), and fused filament fabrication (FFF) may be used with polymer powders or strands to produce plastic constructs. Cellular scaffolds may be formed using bioplotters or 3DP. Although a brief summary follows, many details of a process of melting powdered metal are given in the '332 and '081 Publications. In an example of constructing a tangible structure from a model build geometry using metal powder, a layer of metal powder may be deposited onto a substrate. The substrate may be a work platform, a solid base, or a core, with the base or core being provided to possibly be an integral part of the finished product.

The metal powder may be but is not limited to being made from any of titanium, a titanium alloy, stainless steel, magnesium, a magnesium alloy, cobalt, a cobalt alloy including a cobalt chrome alloy, nickel, a nickel alloy including a nickel titanium alloy, tantalum, and niobium. In some embodiments, individual layers of metal may be scanned using a directed high energy beam, such as a continuous or pulsed laser or e-beam system to selectively melt the powder, i.e., melt the powder in predetermined locations. Each layer, or portion of a layer, is scanned to create a plurality of predetermined porous or mesh physical constructs, and when necessary predetermined solid constructs, by point exposure to the energized beam. This leads to the production of linear, curvilinear, or other shaped struts that correspond to the segments described previously herein and eventually to a porous or mesh physical construct, as will be described below. Successive layers are deposited onto previous layers and also are scanned. The scanning and depositing of successive layers continues the building process of the predetermined porous geometries. As disclosed herein, continuing the building process refers not only to a continuation of a porous or mesh physical construct from a previous layer but also a beginning of a new porous or mesh physical construct as well as the completion of the current porous or mesh physical construct.

In alternative arrangements, non-metallic materials may be used in such additive layer manufacturing processes. These materials may include implantable plastics including but not limited to wax, polyethylene (PE) and variations thereof, polyetheretherketone (PEEK), polyetherketone (PEK), acrylonitrile butadiene styrene (ABS), silicone, and cross-linked polymers; bioabsorbable glass, ceramics, and biological active materials such as collagen/cell matrices. Composites of any of these materials or the metals described previously herein may be made as a combination with any of bone cement, bone, soft tissue, and cellular matrices and tissue cells.

A component structure or sub-structure thereof produced by the approaches herein may be porous and if desired, the pores can be interconnecting to provide an interconnected porosity. In some embodiments, the amount and location of porosity may be predetermined, and preferably lie in the range 50% to 90% as being suitable when used as a bone ingrowth surface, and 20% to 90% as being suitable for polymer interlock surfaces. This also applies to cases where the outer porous section of a medical device is connected to host bone with bone cement or bone type adhesives for example.

When physical constructs are produced using a laser or electron beam melting process, a prefabricated base or core may act as a substrate building physical constructs. Such bases may be made of any of the materials described previously herein for use in the additive layer manufacturing processes. In some instances, such materials may be different than the materials for the successive layers built during the additive layer manufacturing processes. Thus, a mixture of desired mixed materials can be employed. By way of example, porous layers can be built onto an existing article, which itself may be porous or solid, made from any of cobalt chrome, titanium or alloy, stainless steel, tantalum or niobium. In this example, the existing article may be an orthopaedic implant. In such a manner, the approaches described herein may be exploited to produce commercially saleable implants with bone in-growth structures having porous surfaces with a predetermined scaffold structure. The constructed medical implant, which may correspond to the mesh geometries described previously herein, may have a porosity and architecture optimized, to create very favorable conditions so that bone in-growth takes place in a physiological environment and the overall outcome favors long-term stability.

Because a laser or electron beam melting process may not require subsequent heat treatment or the temperature at which this heat treatment occurs is lower than any critical phase change in the material, the initial mechanical properties of any base metal to which a porous structure is applied may be preserved.

The equipment used for additive layer manufacturing of implants could be one of many currently available, including but not limited to those manufactured by Renishaw, SLM Solutions, Realizer, EOS, Concept Laser, Arcam and the like. The laser or electron beam may also be a custom-produced laboratory device.

Figure 6:
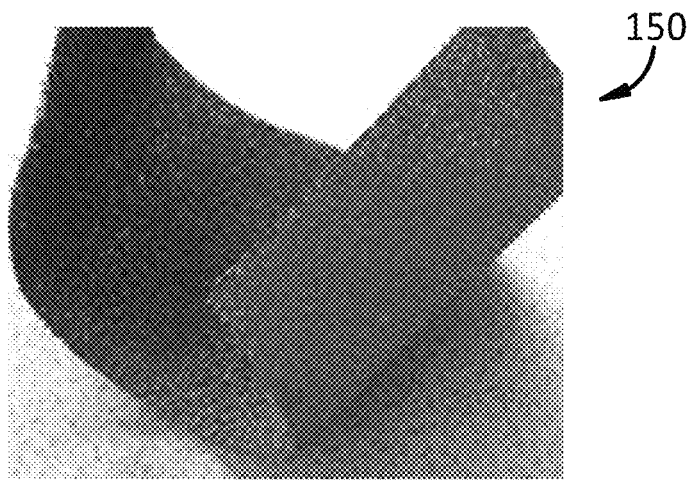
FIG. 6 is an example of a mesh sheet in accordance with another embodiment.

As shown in FIG. 6, mesh sheet 150 was produced by melting successive layers of metal powder. To produce physical constructs of this form, with reference to FIG. 3, spots corresponding to ends 111 of curvilinear segments 110 and ends 122 of curvilinear segments 120 may be formed during production of one layer of an intended physical structure corresponding to porous CAD volume 100A, spots corresponding to ends 121 of curvilinear segments 120 and ends 112 of curvilinear segments 110 may be formed using a high energy beam during production of another layer of the intended physical structure corresponding to porous CAD volume 100A, and spots corresponding to portions of curvilinear segments 110 and portions of curvilinear segments 120 may be formed during production of other layers of the intended physical structure corresponding to porous CAD volume 100A. Such spots may be formed using an SLS or SLM process in which when a laser is the high energy beam, the powder particles may have a diameter on the order of between and including 5 and 50 µm, and when an electron beam is the high energy beam, the powder particles may have a diameter on the order of between and including 75 and 150 µm. In a similar manner, the geometries of the porous CAD volumes 100, 200A, and 200B as described previously herein may be formed into mesh sheets. Similar constructions may be but are not limited to being formed using any of the other additive manufacturing processes discussed previously herein, including 3DP, SLA, FFF, and digital light processing (DLP).

Again referring to FIG. 6, mesh sheet 150 is made of titanium. Due to the rigidity of the material, mesh sheet 150 has been trimmed to size by a pair of scissors, producing little debris relative to other devices that require modification from a Midas Rex, such as with cone and sleeve augments. Mesh sheet 150 is malleable due to its minimal thickness and thus has been curled into shape. As shown, mesh sheet 150 has also been coated with a PERI-APATITE® hydroxyapatite coating but remains porous to promote bone in-growth. Although the surfaces of mesh sheet 150 are relatively rough, in alternative arrangements, at least one surface of the mesh sheet may be smooth to prevent irritation to surrounding soft tissues. Such surface may be produced using the techniques taught in U.S. Patent Application Publication No. 2013/0268085, now U.S. Pat. No. 9,180,010 ("the '010 Patent"), incorporated by reference in its entirety herein.

Referring to the illustrations of FIGS. 7A-7D, the CAD modeling and layered additive manufacturing process in accordance with the present technology can be used to form physical structures having a plurality of mesh sheets 350A, 350B, 350C, 350D connected together by one or more links 355. The mesh sheets may be but are not limited to being formed of segments corresponding to segment geometries of porous CAD volumes, such as but not limited to any of porous CAD volumes 100, 100A, 200A, and 200B or may be formed of a series of overlapping and underlapping strips prepared using a CAD model without the use of repeating unit cells, as described previously herein. During preparation of any such woven mesh patterns, the overlapping and underlapping segments or strips may be fused together at selected intersections or "cross-over" areas of the strips to impart more rigidity to the mesh at the fused areas.

Figure 7A:
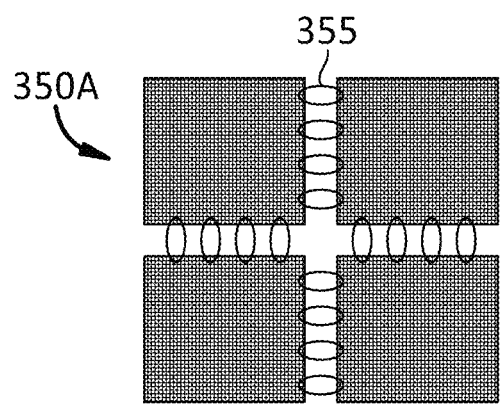
FIGS. 7A-7D are illustrative profile views of mesh sheets in accordance with another embodiment.
Figure 7B:
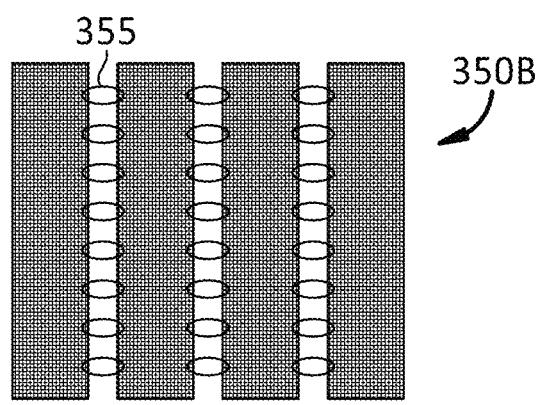
Figure 7C:
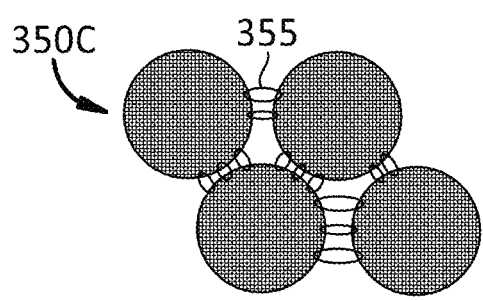
Figure 7D:
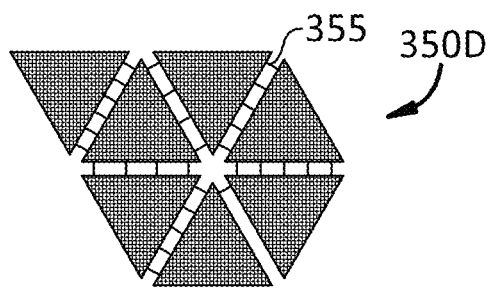

In such arrangements, the physical mesh sheet constructs may have but are not limited to having a square profile such as in FIG. 7A, a rectangular profile such as in FIG. 7B, a circular profile such as in FIG. 7C, and a triangular profile such as in FIG. 7D. Links 355, which may correspond to link geometries created within a CAD model, may have closed perimeters as shown, or may have open perimeters. Links 355 may have profiles which may be but are not limited to being circular, triangular, hexagonal, and octagonal. As in the examples of FIGS. 7A-7D, links 355 may extend through openings defined by adjacent segments or strips along edges of physical mesh sheet constructs, such as mesh sheets 350A-D.

When forming such physical structures using any layered additive manufacturing process, a predetermined thickness of mesh sheets 350A, 350B, 350C, 350D and of links 355, corresponding to a slice height of a CAD model inputted into a layered additive manufacturing device, may be generated during production of a single layer of an intended physical structure. In this manner, a portion of each of mesh sheets 350A-D and of each of links 355 shown in FIGS. 6A-6D may be produced during formation of a single layer of the physical structures shown in FIGS. 7A-7D.

Figure 8:
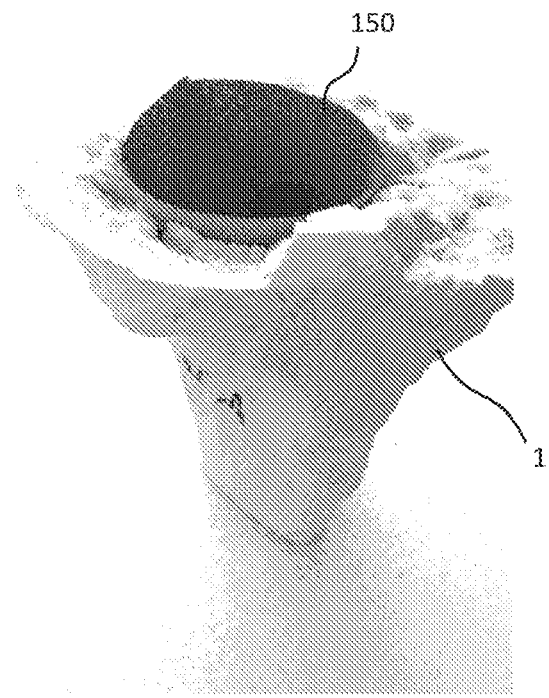
FIG. 8 is an example of an application of the mesh sheet of FIG. 6.

There are a number of useful applications for the mesh sheets. As shown in FIG. 8, mesh sheet 150 is in the form of a foil such that the mesh sheet may be press fit into a bony void space, such as that shown in bone 1. As shown, mesh sheet 150 has a coated outer surface that promotes mechanically strong bone in-growth and also has a coated inner surface that provides a textured surface to rigidly fix bone cement, when such cement is applied to the inner surface, in the shape of the inner surface of the mesh sheet. For this type of application, mesh sheet 150 has a maximum allowable pore size to prevent seepage of the cement through the mesh sheet causing undesirable bone-to-cement contact. Below a specific pore size, bone cement is at its "dough phase," a phase in which the cement is viscous enough not to stick to a surgeon's glove, does not penetrate through the mesh. Randomizing the unit cell structures within a porous CAD volume may also limit the flow of bone cement.

Figure 9A:
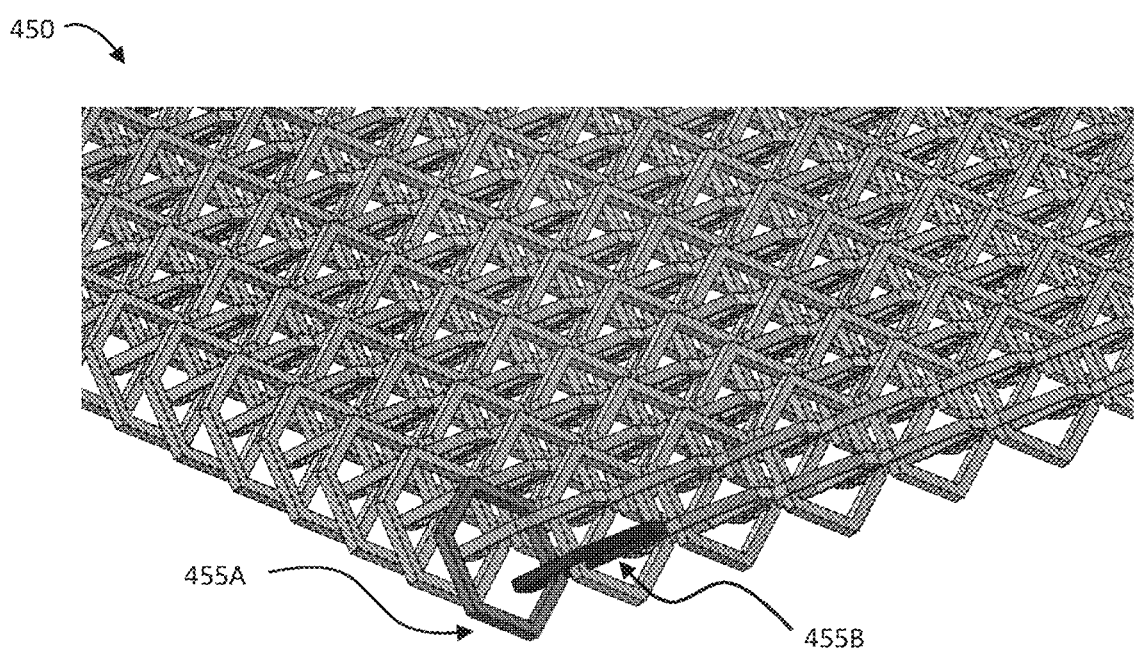
FIGS. 9A and 9B are perspective views of a three-dimensional model representation of portions of a mesh sheet in accordance with an embodiment.
Figure 9B:
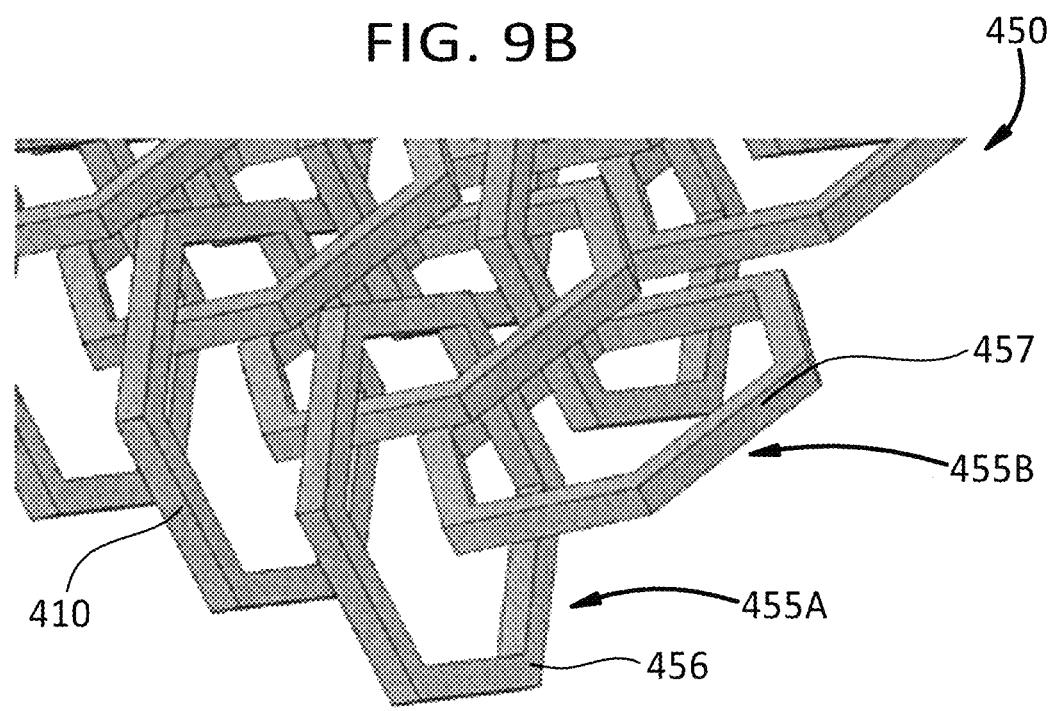

As shown in FIGS. 9A and 9B, a CAD model of mesh sheet geometry 450 includes a set of connected link geometries 455A oriented in a vertical direction and link geometries 455B oriented in a horizontal direction. A "chain link" mesh sheet corresponding to this CAD model including a set of connected links may be formed using any of the additive layer manufacturing processes described previously herein in accordance with the present technology.

Referring again to FIGS. 9A and 9B, as shown, each link geometry 455A, 455B is a substantially planar open hexagon formed of six connected segments 410 which are connected to a plurality of other link geometries 455A, 455B. Each link geometry 455A, 455B has a closed perimeter such that a physically produced link corresponding to this link geometry may not be separated from other links to which the physically produced link is connected without severing one of the connected links. In alternative arrangements, at least some physically produced links may have an opening through their perimeters such that links to which a link is connected may be removed through the opening. In instances in which the opening of an open perimeter is too small, a link having such an opening may be deformed to widen such opening.

Figure 9C:
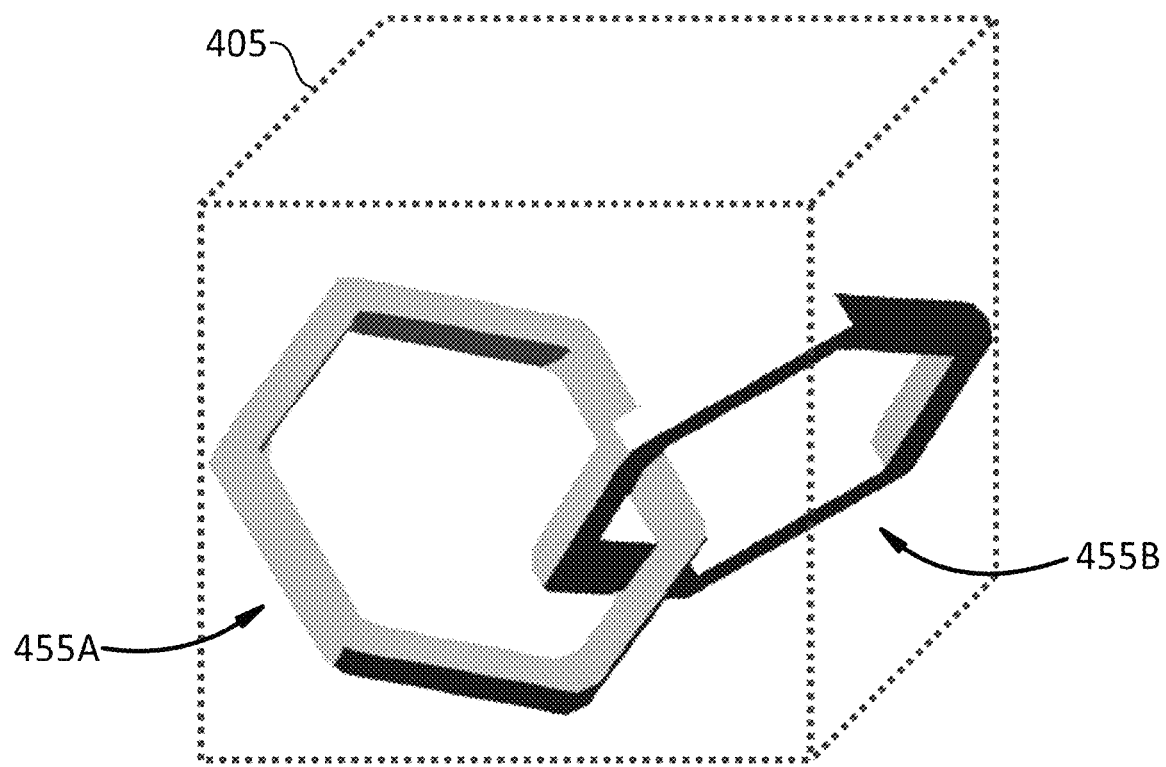
FIG. 9C is a perspective view of a three-dimensional model representation of a unit cell for use in preparing the three-dimensional model representation of the portions of the mesh sheet shown in FIGS. 9A and 9B.

In one arrangement of forming mesh sheet geometry 450, each link geometry within a CAD model may be modeled individually without the use of tessellated unit cells. In an alternative arrangement as shown in the example of FIG. 9C, unit cell 405 may be tessellated to form mesh sheet geometry 450. As shown, unit cell 405 includes one link geometry 455A interlocked with one link geometry 455B. With reference to FIGS. 9A and 9B, upon tessellation of unit cell 405 to form a porous CAD volume containing mesh sheet geometry 450, each link geometry 455A of one unit cell becomes interlocked with link geometries 455B of adjacent unit cells, and each link geometry 455B of one unit cell becomes interlocked with link geometries 455A of adjacent unit cells. In this manner, in the example of FIGS. 9A and 9B, each link geometry 455A becomes interlocked with four link geometries 455B and each link geometry 455B becomes interlocked with four link geometries 455A.

In the example of FIGS. 9A and 9B, planes defined by a widest dimension of interlocked link geometries 455A, 455B are arranged orthogonally to each other. Interlocked link geometries 455A, 455B are spaced apart a slight distance from each other and have the same size. In alternative arrangements, interlocked link geometries may be set at any of non-orthogonal angles to each other, different spacings relative to each other, and different sizes relative to each other. Through these variations, any of the porosity and flexibility of mesh sheets corresponding to modeled mesh sheet geometries may be varied. In some alternative arrangements, unit cells, such as unit cells 405, may be offset by a distance that is different than the spacing between interlocked link geometries of each unit cell to form a non-uniform mesh geometry. In some alternative arrangements, some regions of a mesh geometry may be different in any dimension than other regions of a mesh sheet geometry to form varying porosity, which may be a gradient porosity, within a mesh sheet corresponding to the mesh geometry.

Figure 12A:
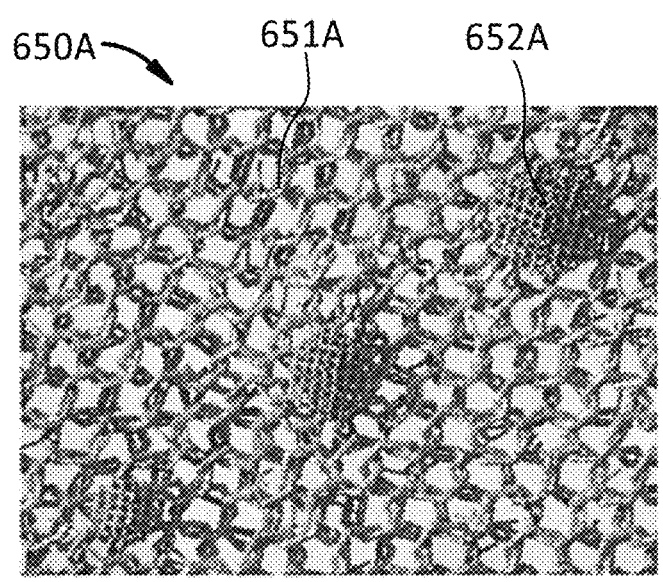
Figure 13A:
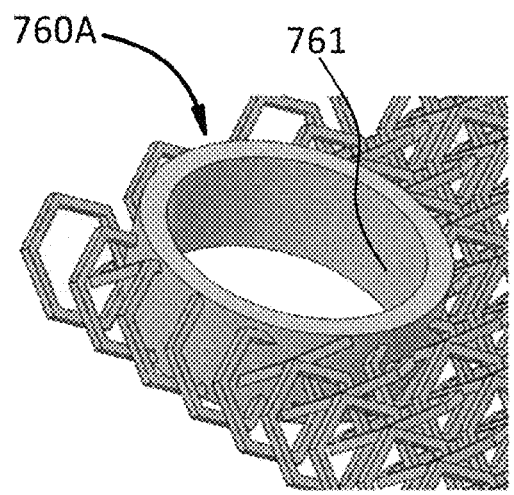
FIG. 13A is a perspective view of a three-dimensional model representation of a portion of a mesh sheet in accordance with an embodiment.
Figure 13B:
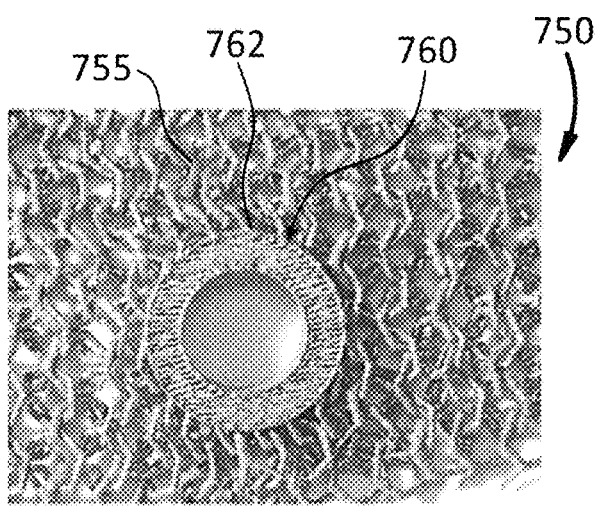
FIG. 13B is an example of an application of the mesh sheet of FIG. 13A.

When forming a physical structure corresponding to mesh sheet geometry 450, which may be a mesh sheet or other flexible construct such as those shown in FIGS. 12A and 13B described further herein, a bottom portion of links, such as a bottom portion of a link corresponding to vertices 456 of link geometries 455A, may be formed during preparation of a first layer of the physical structure of the mesh sheet geometry by an additive layer manufacturing device. Successive layers of the physical structure may then be prepared by the additive layer manufacturing device to form complete links corresponding to link geometries 455A, 455B in which links corresponding to link geometries 455A define planes that are aligned vertically, i.e., orthogonally, with respect to a substrate on which the physical structure is formed, and links corresponding to link geometries 455B define planes that are aligned horizontally, i.e., parallel, with respect to the substrate. In this manner, and with reference to FIGS. 9A-9C, during preparation of the successive layers, only portions of links corresponding to width 457 along opposite sides of the vertically-aligned hexagonal links 455A may be formed in the layers forming links corresponding to horizontally-aligned hexagonal links 455B.

The size of the segments forming the links, which correspond to the segment geometries forming the link geometries, such as link geometries 455A, 455B, the shape of any of the segments and the links, and thus the sizes of pores defined by the links may be adjusted to suit a particular application of a physical construct such as a mesh sheet. Such variables may be used to control flexibility, range of motion, and strength of an overall construct, such as a mesh sheet as well as to control any of the amount of tissue ingrowth and the egress of contained materials, with pore size and shape optimized to pressurize doughy bone cements or morselized bone graft materials. To achieve these goals, the pore sizes preferably should be greater than 300 μm and strut sizes preferably should be greater than 100 μm. In this manner and depending on material choice, the physical construct may have any of a relatively high tensile strength, low flexion and compressive stiffness, variable tensile stiffness, variable stiffness, and ductility.

Link geometries, and thus their corresponding links in physical constructs, may be but are not limited to being in the shape of any of a hexagon, a circle, an ellipse, a square, a triangle, a rectangle, and any combination of these shapes. Links may be planar, such as links corresponding to link geometries 455A, 455B in the example of FIGS. 9A-9C, as well as non-planar, in which links may extend in three dimensions, e.g., a kinked hex design. In some arrangements, the ratio of strut size to pore size for a given shape of strut corresponding to a segment in a CAD model may be varied to influence flexibility, range of motion, and strength in some or all directions. The ratio of links connected to each link may be adjusted throughout all or a portion of a flexible construct such as a mesh sheet. For example, in a preferred arrangement, a connected link ratio of 4:1 may be used to make a uniform sheet construct. In another example, a connected link ratio of 2:1 may be used to make a chain construct, and in yet another example, odd-numbered connected link ratios may be used to create discontinuous flexible constructs.

Physical constructs formed using link geometries may have a graded porosity by varying any of link size and shape within the same construct to provide for any of variable flexibility, variable range of motion, and variable strength throughout the construct. In some arrangements, physical constructs formed using the link geometries may be formed with anisotropy by varying any of link size and shape, by varying strut size and shape, or by selectively fusing some links to each other. Links may be coated with various biocompatible substances, such as but not limited to hydroxyapatite, to facilitate biological bone ingrowth. Links may also coated to minimize wear and also with antibiotic eluting coating in order to treat infection.

Following formation of a flexible construct such as chain link mesh constructs, mechanical and flexural properties may be adjusted by various post-processing techniques. In one arrangement, the flexible construct may be rolled into a cylinder, increasing the yield strength of the construct along the axis of the cylinder. In another arrangement, one flexible construct may be stacked onto or nested within another flexible construct such that the stacked or nested constructs interact to constrain or augment each other. In some applications, the flexible construct may be shaped, such as by rolling or flattening, such that the construct does not transmit compressive loads.

Figure 10A:
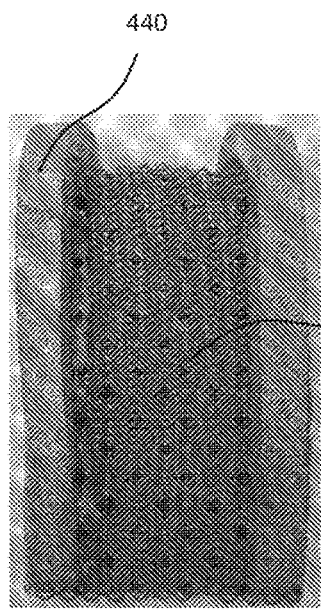
FIGS. 10A-12C are views of applications of mesh sheets in accordance with embodiments.
Figure 10B:
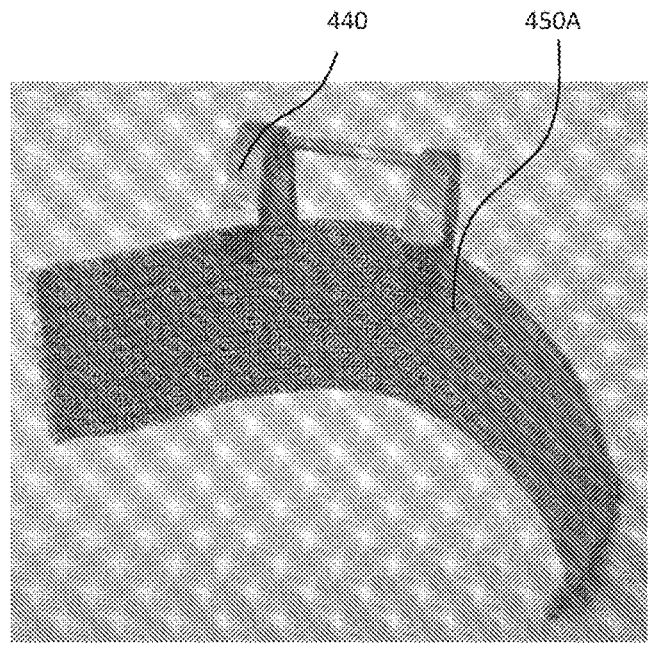
Figure 10C:
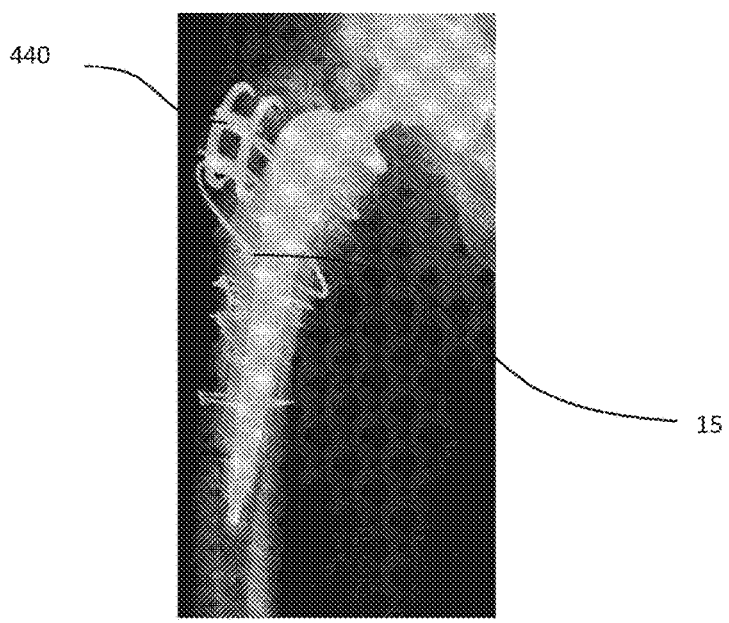

As shown in FIGS. 10A-10C, in one application of the chain link mesh sheets, mesh sheet 450A, which has been formed using an additive layer manufacturing process based on a mesh sheet geometry substantially similar to mesh sheet geometry 450, acts as a trochanteric gripper which may be placed over the trochanter of a femur to provide an ingrowth surface Shell 440 is then placed over mesh sheet 450A and around the trochanter. Cables 15, which as shown are cerclage wires, may be wrapped around mesh sheet 450A to hold mesh 450A in place or, alternatively, may be wrapped around shell 440, such as by being passed around or through a thickness of spaced-apart arms of shell 440, to hold the assembly of the shell and mesh sheet 450A in place.

Figure 11:
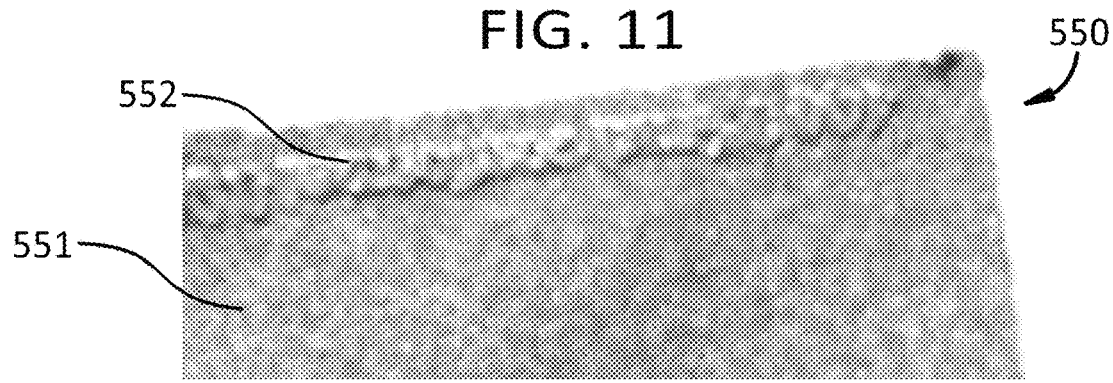

Referring now to FIGS. 11-17D, the chain link and mesh sheets may be produced along with additional features by any of the additive layer manufacturing processes described previously herein. As shown in FIG. 11, mesh sheet 550 includes a woven mesh pattern 551 and an alphanumeric pattern 552 fused to the woven mesh pattern, in which the alphanumeric pattern is formed substantially as shown and described in the '010 Patent, using an additive layer manufacturing device. During preparation of mesh sheet 550, successive layers are added to basic mesh pattern 551 to form alphanumeric pattern 552. In this manner, alphanumeric pattern may be used as product identifiers.

Figure 12B:
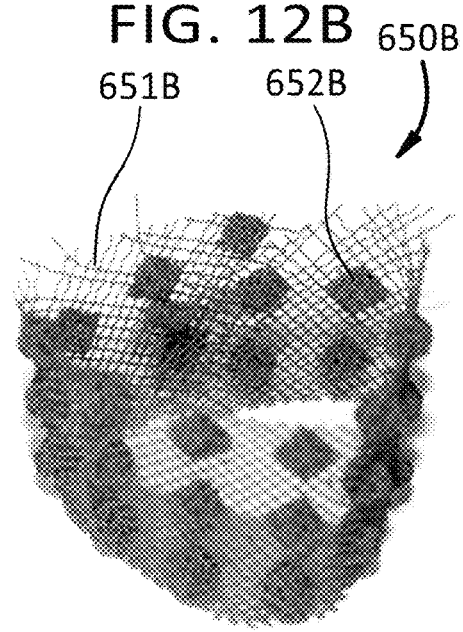
Figure 12C:
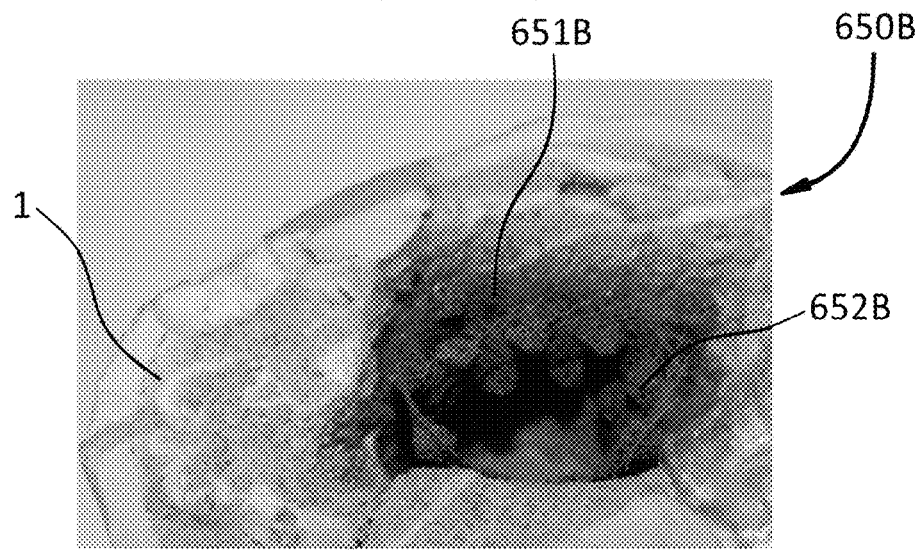

As shown in FIGS. 12A-12C, mesh sheets may include porous attachment components. In the example of FIG. 12A, mesh sheet 650A includes chain link pattern 651A and a porous attachment component 652A fused to the chain link pattern at spaced-apart regions of the chain link pattern. In the example of FIGS. 12B and 12C, mesh sheet 650B includes woven mesh pattern 651B and porous attachment component 652B. In these examples, porous attachment components 652A, 652B have been added to both sides of woven mesh pattern 651B during an additive layer manufacturing process. Porous attachment components may be lattice structures such as those disclosed in the '332 Publication as in the example shown, or may be in the form of woven mesh or chain link patterns. In applications for facilitating biological attachment of bone, porous attachment components, such as porous attachment components 652A, 652B, may be used and may have a pore size in the range of approximately 100-1000 μm and a porosity which preferably may be at least 50%. Porous attachment components designed to function as scaffold cells for biological regeneration preferably may have a pore size greater than 100 μm and a porosity greater than 55%. In alternative arrangements (not shown), porous attachment components may be other types of porous structures including but not limited to woven mesh or chain link mesh structures, which may have a pore size and porosity that is different than the mesh, chain link pattern, or other pattern, which may be porous or non-porous, to which the porous attachment components may be attached.

As shown in FIG. 12C, mesh sheet 650B, acting as a foil, may be rolled into a cylindrical shape and placed or pressed into a bony void space, such as in the base of a tibia bone 1, as in this example. Although not shown, mesh sheet 650A could be placed into a bony void space in a similar fashion. In such arrangements, bone cement then may be added inside of the cylindrically-shaped mesh sheets 650A, 650B. In this manner, mesh sheets 650A, 650B may promote better mechanical rigidity between live bone and bone cement.

As shown in FIGS. 13A and 13B, eyelet 760 may be integrated into the mesh sheets, chain link mesh sheet 750 in this example, during an additive layer manufacturing process. Eyelet 760 may be modeled as solid eyelet geometry 760A as shown in FIG. 13A having inner perimeter 761, which may act as a through bore. Depending on the parameter settings of the additive layer manufacturing device, eyelet 760 may be substantially solid or somewhat porous through its thickness, upon production of the physical structure of the eyelet, as shown in FIG. 13B. Mesh sheet 750 was built in its entirety in layers using an additive layer manufacturing process. As shown, some of hexagonal links 755 of mesh sheet 750 abut outer perimeter 762 of eyelet 760. Some of such links 755 have open perimeters in which ends of the open perimeters of the links are fused to eyelet 760. Eyelet 760 may be but is not limited to being used for screw, wire, or cable attachment of mesh sheet 750 to other objects, such as bone or other tissue.

Figure 14A:
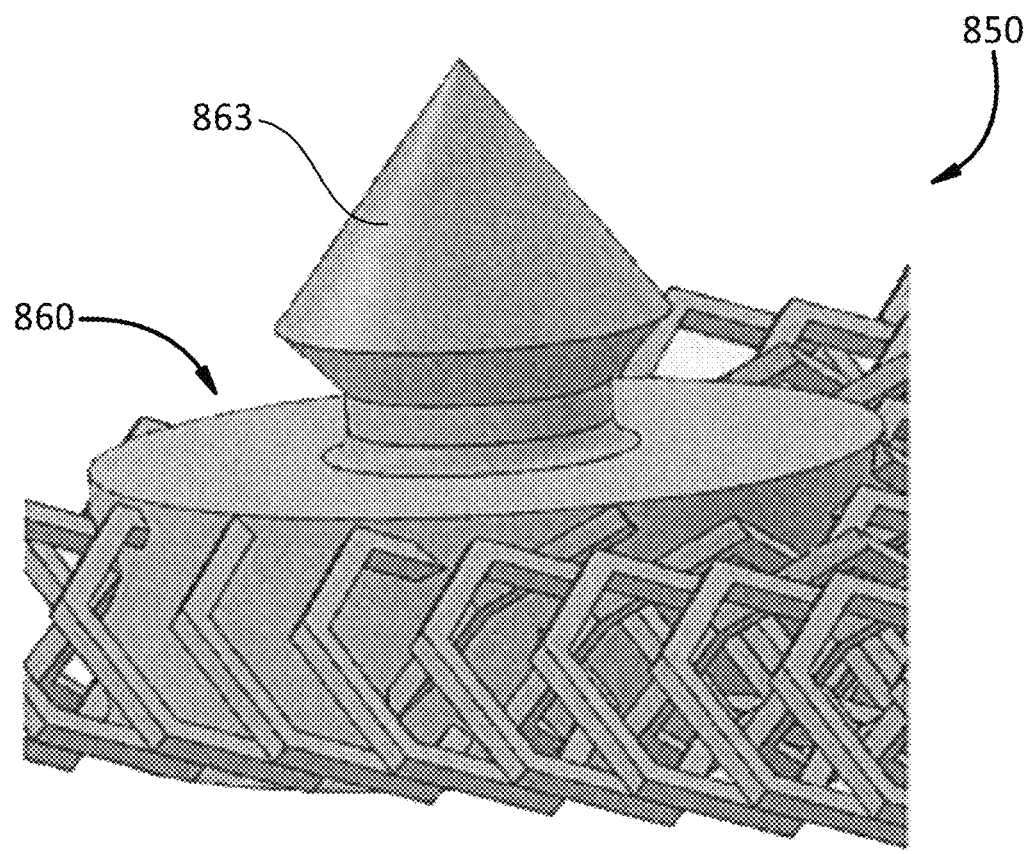
FIGS. 14A-15 are perspective views of three-dimensional model representations of a portion of mesh sheets in accordance with an embodiment.

Referring to FIG. 14A, a CAD model includes mesh sheet geometry 850 including stud geometry 860, which as shown may be a rivet, which may be used to prepare a corresponding mesh sheet with a corresponding stud. The stud corresponding to stud geometry 860 may be formed in the same manner as eyelet 760 and thus may be substantially solid or somewhat porous through its thickness and may be fused to links, with the exception that the stud may include a spike, corresponding to spike geometry 863, and may not include any type of through bore. Such studs may allow the construct to be press fit to itself or other materials, including bone. In some alternative arrangements (not shown), a stud geometry may include a through hole.

Figure 14B:
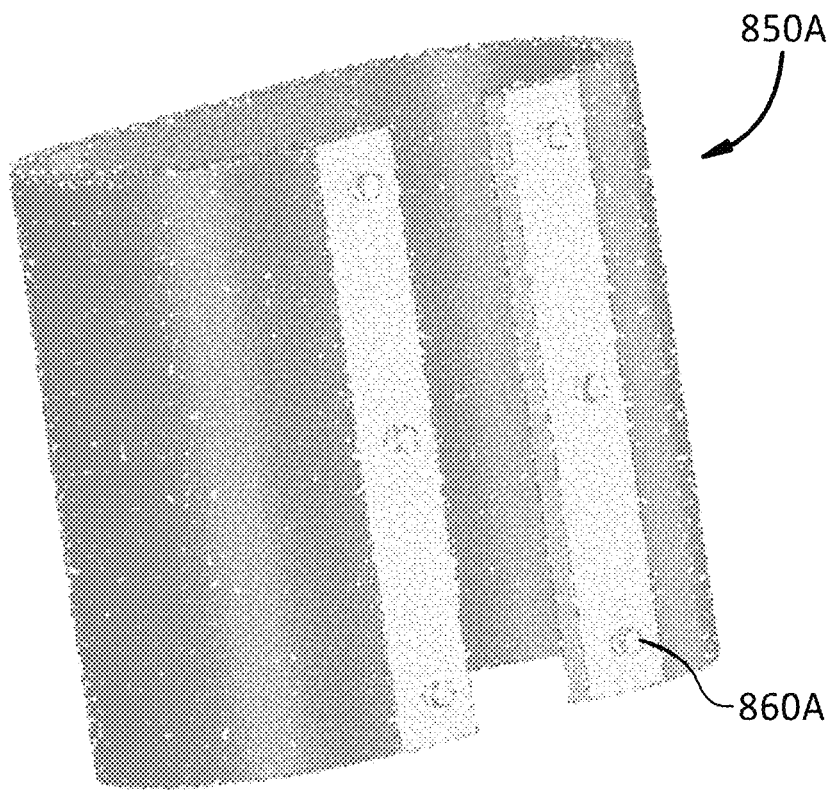
Figure 14C:
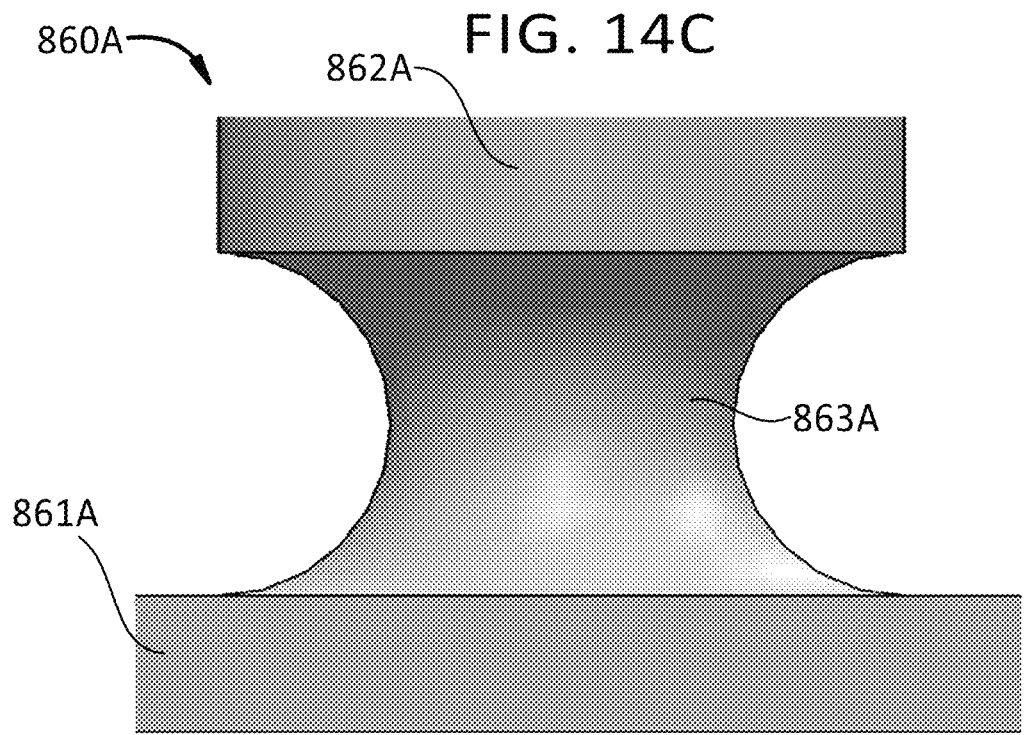

In FIG. 14B, a mesh sheet geometry 850A generated in a CAD model includes a plurality of stud geometries 860A extending outwardly near an edge of the mesh sheet geometry which may be used to prepare a corresponding mesh sheet with a corresponding stud. As shown in FIG. 14C, each stud geometry 860A includes a lower base geometry 861A, an upper base geometry 862A, and an intermediate section geometry 863A between the lower and upper bases. The stud corresponding to each stud geometry 860A may be fused to the rest of the mesh sheet corresponding to mesh sheet geometry 850A at a lower base corresponding to lower base geometry 861A. Referring again to FIG. 14B, studs corresponding to stud geometries 860A may be formed, such as by an additive layer manufacturing process as described previously herein, on opposing ends of a mesh sheet corresponding to mesh sheet geometry 850A such that a cable may be wrapped around an intermediate section of a stud corresponding to stud geometry 860A. In this manner, such a mesh sheet may be tensioned to form a rolled construct, which in some arrangements may be used to enclose other materials, such as but not limited to bone graft material.

Figure 15:
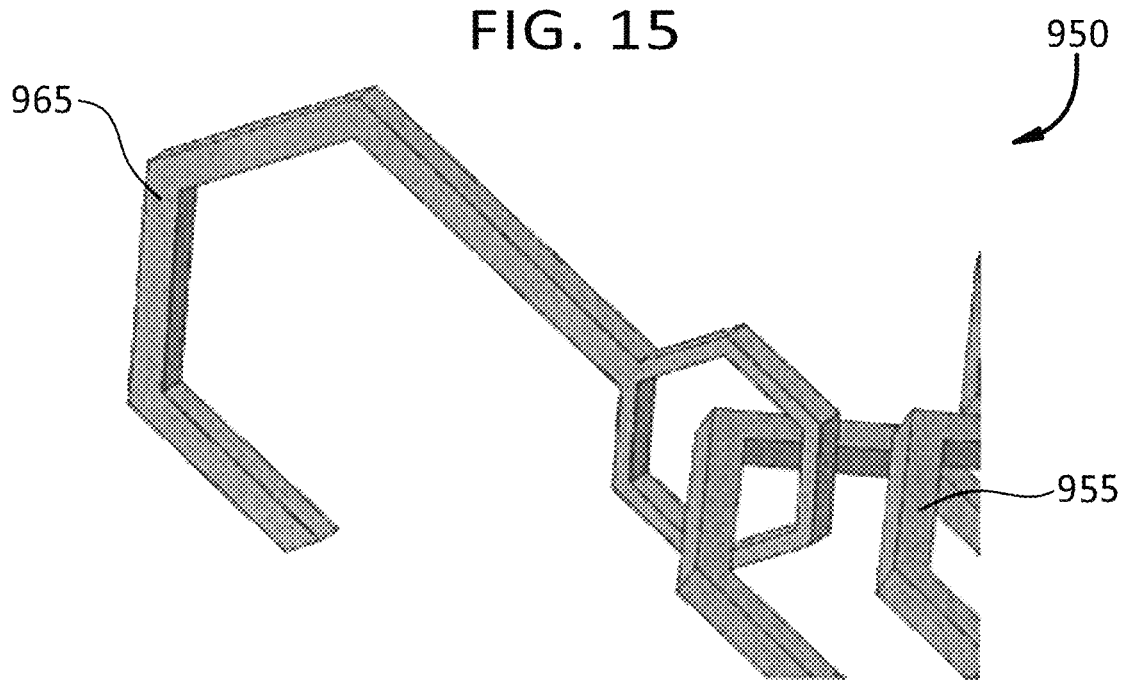

Referring to FIG. 15, a hook may be added to the perimeter of a link as demonstrated by hook geometry 965 attached at a vertex of hexagonal link geometry 955 at an outer perimeter of mesh sheet geometry 950. As shown, hook geometry 965 is in the form of a hexagonal link geometry having an opening at its perimeter. When prepared as a physical structure, the mesh sheet corresponding to mesh sheet geometry 950 may be attached by the hook corresponding to hook geometry 865 to other materials, including but not limited to biological and manufactured materials, or may be attached to another portion of mesh sheet itself to form a wrap or covering.

Figure 16:
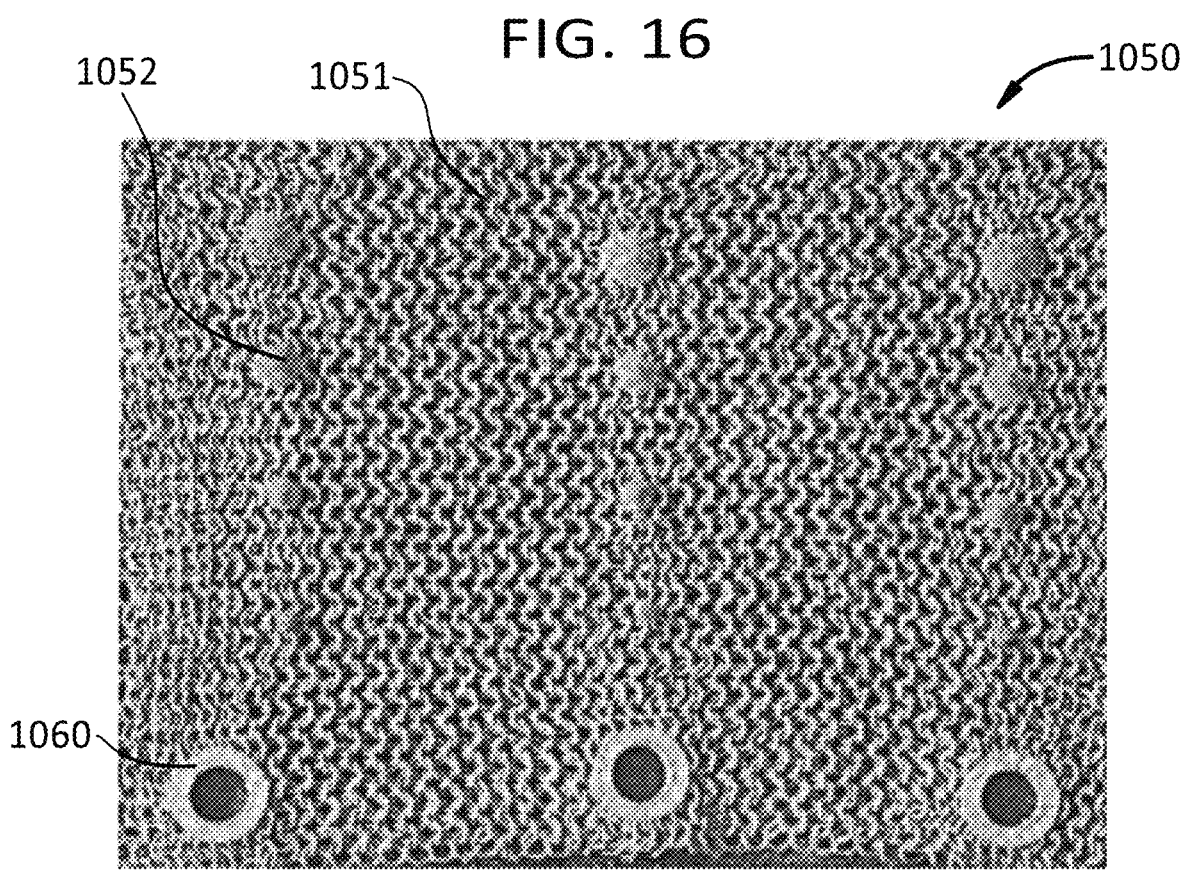
FIG. 16 is an example of a mesh sheet in accordance with an embodiment.

As shown in FIG. 16, mesh sheet 1050 includes a plurality of porous attachment components 1052 and eyelets 1060 fused to chain link mesh pattern 1051. Other combinations of features including but not limited to woven mesh patterns, chain link mesh patterns, porous attachment components, and eyelets may be combined into single mesh sheets in accordance with the present technology. In some arrangements, mesh sheet 1050 may be used in applications designed to facilitate biological attachment of soft tissue, including muscles, tendons, and ligaments. In such arrangements, the porous attachment components preferably may have a pore size greater than 100 μm and a porosity greater than 55%. Using components designed to facilitate attachment of a construct, such as the components described with respect to FIGS. 13A-16, the flexible constructs such as the mesh sheets described herein may be folded and attached to other media or to themselves to form a cavity that can be expanded with a flowing material such as but not limited to bone cement or a combination of bone cement and another device, such as but not limited to a hip or knee replacement, to fill a free-form bone defect.

Figure 17A:
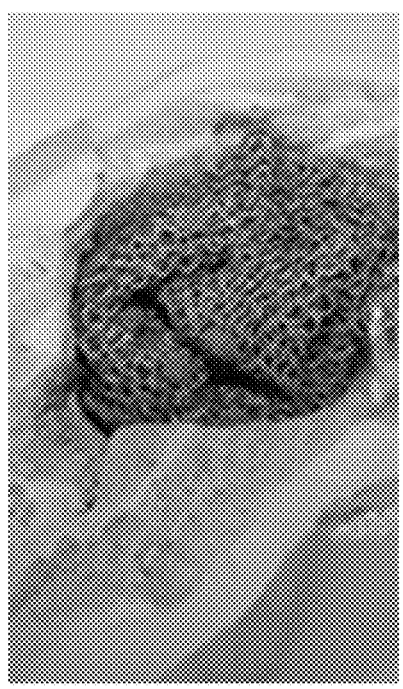
FIGS. 17A-17C are examples of applications of mesh sheets in accordance with embodiments.
Figure 17B:
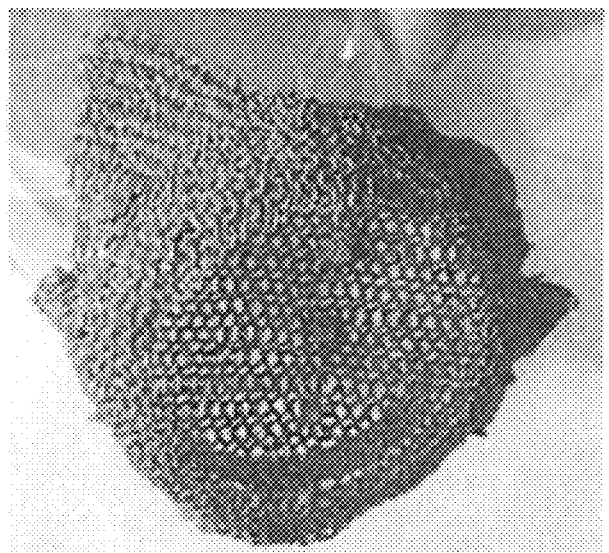
Figure 17C:
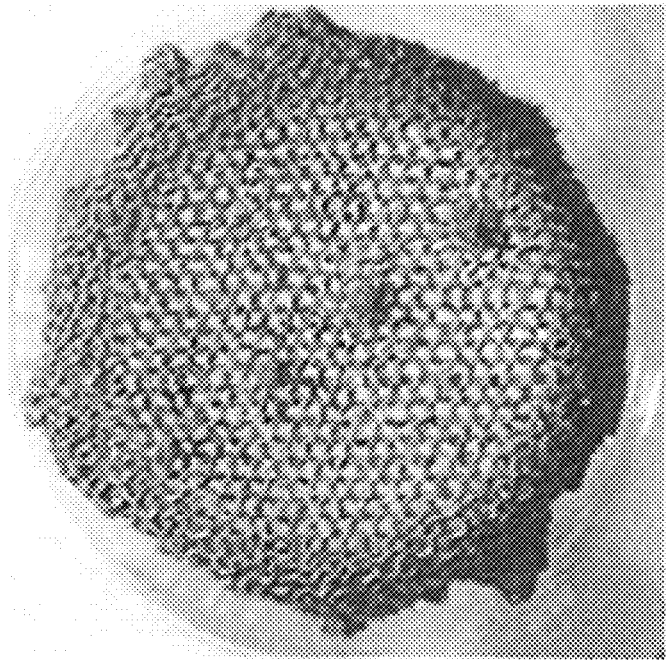

Referring now to FIGS. 17A-17C, chain link mesh sheets provide a network of links that form structures that are both porous and highly flexible. As in the example of FIG. 17A, mesh sheet 1150A may be folded to fill a bony void cavity. As in the examples of FIGS. 17B and 17C, mesh sheets 1150B and 1150C are positioned such that a middle portion of the sheet is substantially flat and an outer portion of the sheet is draped or extended around another object. Components employing the mesh sheet or flexible constructions described previously herein may be completely manufactured in situ or may be partially manufactured for later adjustment in the field to tailor the construct as needed. In some examples, their flexible construction allows the mesh sheets to be folded to contain another material such as bone cement or morselized bone graft where the composite structure of the mesh sheet and the contained material exhibits modified mechanical properties, e.g., enhanced rigidity when bone cement is added.

Referring now to FIGS. 18A and 18B, integrated mesh sheet 1250, which as shown may be termed a "strut graft," was produced using an additive layer manufacturing process such as those described previously herein. Mesh sheet 1250 includes spaced-apart first porous regions 1270 along an entire length of the mesh sheet, spaced-apart second porous regions 1275 across an entire width of the mesh sheet except at the locations of the first porous region 1270, and third porous regions 1280 in all other sections of the mesh sheet. In the example shown, each of porous regions 1270 and 1275 is in the form of chain link mesh patterns, as described previously herein, and has a different porosity and pore size than the other regions. As in the example shown, third porous regions 1280 may have a relatively low porosity such that the third porous regions are substantially rigid. First porous regions 1270 may have the highest porosity among the porous regions 1270, 1275, 1280 such that the first porous regions 1270 of mesh sheet 1250 are the most flexible of the porous regions. In this manner, as shown in FIG. 18B, mesh sheet 1250 may be bent about first porous regions 1270 such that the mesh sheet may be wrapped around bone 10 to aid in bone repair. Second porous regions 1275 may have a higher porosity than third porous regions 1280 but a lower porosity than first porous regions 1270 allowing for third porous regions 1280 to be bent about second porous regions 1275 as well as for compression of mesh sheet 1250 along the second porous regions such that the second porous regions may provide a groove within the mesh sheet when compressed. In this manner, with reference to the radiograph of FIG. 18C, cables 15, which as shown are cerclage wires, may be wrapped around second porous regions 1275 of mesh sheet 1250 such that the second porous regions are compressed to hold the mesh sheet tightly against the bone and to form a groove to hold the longitudinal location of the cables.

In some alternative arrangements of mesh sheet 1250, holes, which may be threaded, may be provided within third porous regions 1280. In this manner, fasteners may be inserted into third porous regions 1280 to facilitate attachment of mesh sheet 1250 to large bone fragments. In some alternative arrangements of mesh sheet 1250, any of the first, second, and third porous regions may be in the form of other porous patterns, such as lattice structures disclosed in any of the '332 Publication, the '081 Publication, the '703 Patent, the '374 Patent, and the '010 Patent.

Figure 19A:
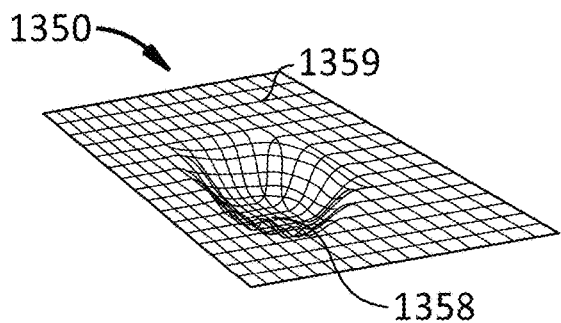
FIGS. 19A and 19B are perspective and side views of a mesh sheet in accordance with an embodiment.
Figure 19B:
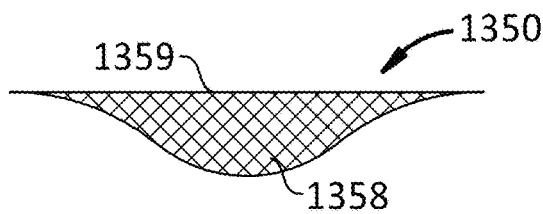
Figure 19C:
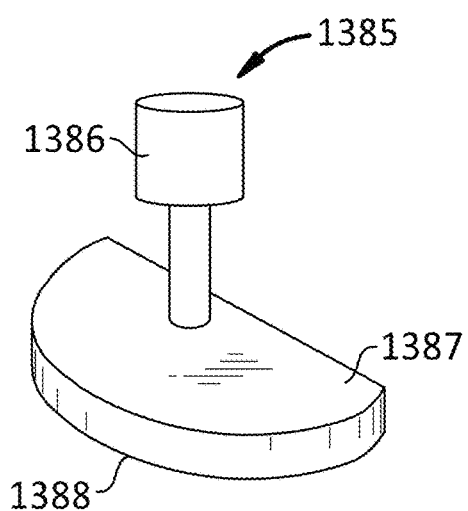
FIG. 19C is a perspective view of a tool for use with the mesh sheet of FIGS. 19A and 19B in accordance with an embodiment.
Figure 19D:
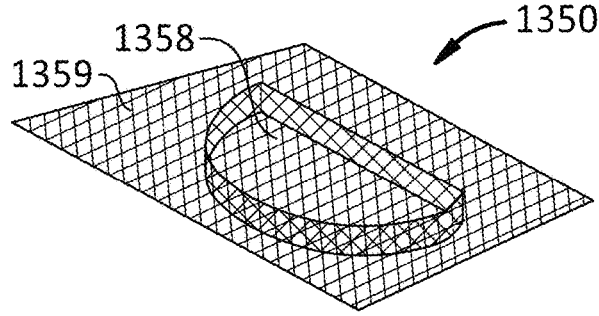
FIGS. 19D and 19E are perspective and side views of the mesh sheet of FIGS. 19A and 19B after deformation of the mesh sheet by the tool of FIG. 19C in accordance with an embodiment.
Figure 19E:
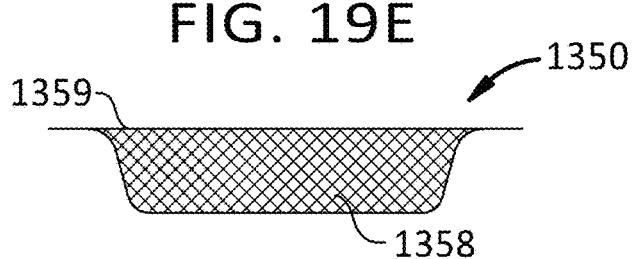

Referring now to FIGS. 19A-19E, mesh sheet 1350 is substantially in the form of a woven mesh sheet pattern similar to the patterns described previously herein, which may be produced using additive layer manufacturing techniques such as those also described previously herein. As shown in FIGS. 19A and 19B, mesh sheet 1350 includes rounded central pocket 1358 extending from flat region 1359 of the mesh sheet. As shown in FIG. 19C, stamp 1385, which as shown is a tibial base stamp, includes handle 1386 and semicylindrical base 1387 having bottom surface 1388 that is substantially flat. With reference to FIGS. 19D and 19E, stamp 1385 may be pressed into mesh sheet 1350 to form a cavity in the mesh sheet. Due to the flexibility of mesh sheet 1350, central pocket 1358 may be stretched such that the mesh sheet has substantially the same form as semicylindrical base 1387 of stamp 1385.

Figure 20A:
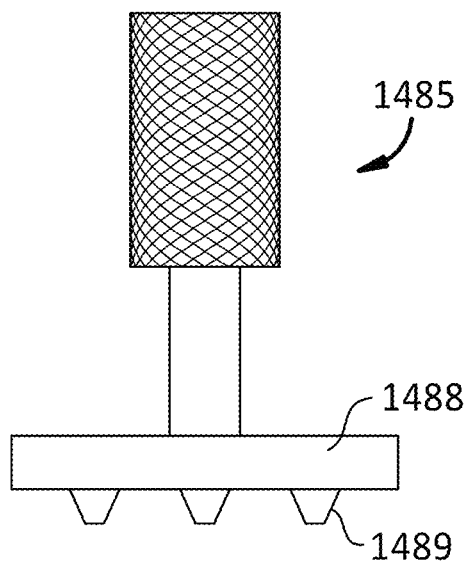
FIG. 20A is a side view of a tool for use with the mesh sheet of FIGS. 19A and 19B in accordance with an embodiment.
Figure 20B:
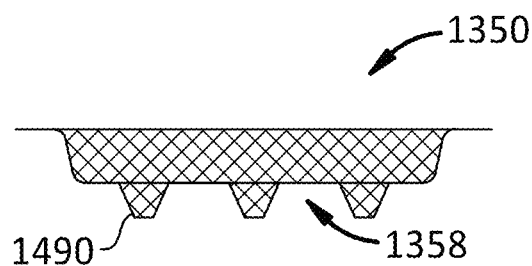
FIG. 20B is a side view of the mesh sheet of FIGS. 19A and 19B after deformation of the mesh sheet by the tool of FIG. 20A in accordance with an embodiment.

As shown in FIGS. 20A and 20B, in an alternative arrangement, stamp 1485 having protrusions 1489 extending from substantially flat bottom surface 1488 of the stamp may be used to press out central pocket 1358 of mesh sheet 1350. In this manner, corresponding protrusions 1490 may be formed on a bottom of central pocket 1358.

Figure 21:
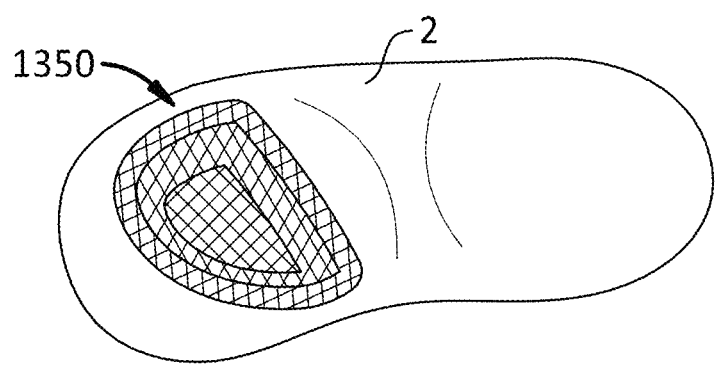
FIG. 21 is a perspective view of an application of the deformed mesh sheets of either of FIGS. 19D and 20B.

As shown in FIG. 21, in one application, stamped mesh sheet 1350 may be placed into a burred out cavity of a bone, such as a tibia 2 as shown, and adhered to the cavity. In this manner, mesh sheet 1350 provides a surface for bone ingrowth to strengthen the mechanical engagement of the bone and bone cement applied into the stamped central pocket 1358 of the mesh sheet and thus aids in preventing subsidence of an onlay or inlay implant placed onto the bone cement and mesh sheet combination within the bone cavity.

There are still other useful applications of the mesh sheet flexible constructs.

It is to be understood that the disclosure set forth herein includes all possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments of the invention, and in the invention generally.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A porous tissue ingrowth implant comprising:
a first mesh sheet;
a second mesh sheet spaced apart from the first mesh sheet; and
a first plurality of metallic links, each of the links of the first plurality of metallic links being attached to a first side of the first mesh sheet and to a first side of the second mesh sheet such that adjacent ones of the links of the first plurality of metallic links are separated by at least one pore defined by either the first mesh sheet or the second mesh sheet,
wherein the first mesh sheet includes pores configured to prevent seepage of a bone cement therethrough.

2. The implant of claim 1, wherein either one or both of the first and the second mesh sheets include chain mail.

3. The implant of claim 1, wherein either one or both of the first and the second mesh sheets are in the form of a woven mesh.

4. The implant of claim 1, wherein at least the first mesh sheet has a rectangular profile, a triangular profile, a hexagonal profile, or a circular profile.

5. The implant of claim 1, wherein each of the links of the first plurality of metallic links forms a closed loop.

6. The implant of claim 1, wherein the first mesh sheet and the second mesh sheet are metallic.

7. The implant of claim 1, further comprising:
a third mesh sheet; and
a second plurality of metallic links, each of the links of the second plurality of metallic links being attached to a second side of the second mesh sheet and to a first side of the third mesh sheet such that adjacent ones of the links of the second plurality of metallic links are separated by at least one pore defined by either the second mesh sheet or the third mesh sheet.

8. The implant of claim 7, wherein each of the links of the second plurality of metallic links extends in a first direction and each of the links of the first plurality of metallic links extends in a second direction transverse to the first direction.

9. The implant of claim 7, wherein each of the links of both the first plurality of metallic links and the second plurality of metallic links extends in the same direction.

10. The implant of claim 7, further comprising:
a fourth mesh sheet;
a third plurality of metallic links, each of the links of the third plurality of metallic links being attached to a second side of the third mesh sheet and to a first side of the fourth mesh sheet such that adjacent ones of the links of the third plurality of metallic links are separated by a pore defined by either the third mesh sheet or the fourth mesh sheet; and
a fourth plurality of metallic links, each of the links of the fourth plurality of metallic links being attached to a second side of the fourth mesh sheet and to a second side of the first mesh sheet such that adjacent ones of the links of the fourth plurality of metallic links are separated by at least one pore defined by either the fourth mesh sheet or the first mesh sheet.

11. The implant of claim 10, wherein the first side of the second mesh sheet is confronting and parallel to the first side of the first mesh sheet, the first side of the third mesh sheet is confronting and parallel to the second side of the second mesh sheet, and the first side of the fourth mesh sheet is confronting and parallel to the second side of the third mesh sheet.

12. The implant of claim 7, wherein the first side of the first mesh sheet defines a first edge, the first and the second sides of the second mesh sheet define a second edge and a third edge, respectively, and the first side of the third mesh sheet defines a fourth edge, wherein the first edge confronts and is parallel to the second edge, and wherein the third edge confronts and is parallel to the fourth edge.

13. The implant of claim 12, further comprising fourth and fifth mesh sheets, wherein edges of the first and the third mesh sheets confront and are parallel to respective edges of the fourth and the fifth mesh sheets.

14. The implant of claim 7, wherein each of the first mesh sheet, the second mesh sheet, and the third mesh sheet define respective vertices pointing towards a common center.

15. A porous tissue ingrowth implant comprising:
a first mesh section;
a first plurality of metallic links;
a second mesh section attached to the first mesh section via the first plurality of metallic links;
a second plurality of metallic links; and
a third mesh section attached to the second mesh section via the second plurality of metallic links,
wherein each of the first, the second, and the third mesh sections have a different porosity than porosities defined by each of the first and the second plurality of metallic links,
wherein the second mesh section is movable relative to the first mesh section about the first plurality of metallic links and the second mesh section is movable relative to the third mesh section about the second plurality of metallic links, and
wherein the first, the second and the third mesh sections are spaced apart, and
wherein the first mesh section includes pores configured to prevent seepage of a bone adhesive therethrough.

16. The implant of claim 15, wherein links of the first plurality of metallic links are attached to a first side of the first mesh section and to a first side of the second mesh section such that adjacent ones of the links of the first plurality of metallic links are separated by a pore defined by either the first mesh section or the second mesh section, and wherein links of the second plurality of metallic links are attached to a second side of the second mesh section and to a first side of the third mesh section such that adjacent ones of the links of the second plurality of metallic links are separated by at least one pore defined by either the second mesh section or the third mesh section.

17. The implant of claim 15, wherein the first plurality of links and the second plurality of links define different porosities.

18. The implant of claim 15, further comprising:
a third plurality of links;
a fourth plurality of links; and
a fourth mesh section attached to the third mesh section via the third plurality of links and attached to the first mesh section via the fourth plurality of links,
wherein the fourth mesh section is movable relative to the third mesh section about the third plurality of links and the fourth mesh section is movable relative to the first mesh section about the fourth plurality of links, and
wherein the first, second, third, and fourth mesh sections are substantially rigid.

19. A porous tissue ingrowth implant comprising:
a first mesh sheet having a first plurality of metallic links;
a second mesh sheet having a second plurality of metallic links; and
a third plurality of metallic links, each of the links of the third plurality of metallic links being attached to the first mesh sheet and to the second mesh sheet and having either one or both of a different shape and a different size than the first and the second pluralities of metallic links, wherein the first and the second mesh sheets are spaced apart.

20. The implant of claim 19, wherein the third plurality of metallic links have a different diameter than the first plurality of metallic links and the second plurality of metallic links.

21. The implant of claim 15, wherein the first, the second, and the third mesh sections are metallic.

22. The implant of claim 19, wherein the first mesh sheet and the second mesh sheet are metallic.

23. The implant of claim 19, wherein the first mesh sheet is formed of segments corresponding to randomized unit cell structures within a porous CAD volume.

24. The implant of claim 1, wherein the first and the second mesh sheets are coplanar.

* * * * *